US007868142B2

(12) United States Patent
Hatakeyama et al.

(10) Patent No.: US 7,868,142 B2
(45) Date of Patent: Jan. 11, 2011

(54) PROTEIN, METHOD FOR IMMOBILIZING PROTEIN, STRUCTURE, BIOSENSOR, NUCLEIC ACID, VECTOR AND KIT FOR DETECTING TARGET SUBSTANCE

(75) Inventors: Satoru Hatakeyama, Kawasaki (JP); Takeshi Imamura, Chigasaki (JP); Hidenori Shiotsuka, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 556 days.

(21) Appl. No.: 11/869,711

(22) Filed: Oct. 9, 2007

(65) Prior Publication Data
US 2008/0187461 A1 Aug. 7, 2008

(30) Foreign Application Priority Data
Oct. 13, 2006 (JP) ............................. 2006-280423
Oct. 1, 2007 (JP) ............................. 2007-257738

(51) Int. Cl.
*C07K 16/00* (2006.01)
*G01N 33/53* (2006.01)
*C12M 1/34* (2006.01)
*C12N 5/16* (2006.01)
*C12N 15/00* (2006.01)

(52) U.S. Cl. ............... 530/389.8; 530/388.9; 530/391.9; 530/387.3; 435/345; 435/7.1; 435/7.92; 435/287.2; 435/326; 435/320.1

(58) Field of Classification Search ....................... None
See application file for complete search history.

(56) References Cited

U.S. PATENT DOCUMENTS

| 4,816,567 | A | 3/1989 | Cabilly et al. ............... 530/387 |
| 5,665,597 | A | 9/1997 | Imamura et al. ......... 435/253.3 |
| 5,679,568 | A | 10/1997 | Imamura et al. ......... 435/262.5 |
| 5,693,527 | A | 12/1997 | Imamura ..................... 435/262 |
| 5,803,664 | A | 9/1998 | Kawabata et al. ........... 405/128 |
| 5,807,736 | A | 9/1998 | Kozaki et al. ............ 435/262.5 |
| 5,854,059 | A | 12/1998 | Kozaki et al. ............... 435/262 |
| 5,858,802 | A * | 1/1999 | Chai-Gao et al. ........... 436/524 |
| 5,863,789 | A | 1/1999 | Komatsu et al. ............. 435/262 |
| 5,945,331 | A | 8/1999 | Kozaki et al. ............... 435/262 |
| 5,962,305 | A | 10/1999 | Mihara et al. ............ 435/262.5 |
| 5,993,658 | A | 11/1999 | Kato et al. ................... 210/611 |
| 6,004,772 | A | 12/1999 | Imamura et al. .............. 435/34 |
| 6,017,746 | A | 1/2000 | Imamura et al. ........... 435/252.1 |
| 6,096,530 | A | 8/2000 | Kato et al. ............... 435/253.3 |
| 6,319,706 | B1 | 11/2001 | Kawaguchi et al. ....... 435/293.1 |
| 6,472,191 | B1 | 10/2002 | Yano et al. ................... 435/189 |
| 6,479,621 | B2 | 11/2002 | Honma et al. ............... 528/361 |
| 6,586,562 | B2 | 7/2003 | Honma et al. ............... 528/361 |
| 6,649,381 | B1 | 11/2003 | Honma et al. ............... 435/135 |
| 6,660,516 | B1 | 12/2003 | Imamura et al. .......... 435/252.8 |
| 6,686,439 | B2 | 2/2004 | Kenmoku et al. ............ 528/272 |
| 6,803,444 | B2 | 10/2004 | Suzuki et al. ................ 528/361 |
| 6,808,854 | B2 | 10/2004 | Imamura et al. ............. 430/110 |
| 6,828,074 | B2 | 12/2004 | Yano et al. ................ 430/109.1 |
| 6,855,472 | B2 | 2/2005 | Imamura et al. .......... 430/109.4 |
| 6,858,367 | B2 | 2/2005 | Yano et al. .................... 430/109 |
| 6,858,417 | B2 | 2/2005 | Yano et al. .................... 435/189 |
| 6,861,496 | B2 | 3/2005 | Kenmoku et al. ............. 528/272 |
| 6,861,550 | B2 | 3/2005 | Honma et al. ................. 560/53 |
| 6,864,074 | B2 | 3/2005 | Yano et al. .................... 435/189 |
| 6,867,023 | B2 | 3/2005 | Honma et al. ................ 435/135 |
| 6,869,782 | B2 | 3/2005 | Kenmoku et al. ............ 435/130 |
| 6,908,720 | B2 | 6/2005 | Kenmoku et al. ............. 430/97 |
| 7,169,598 | B2 | 1/2007 | Honma et al. ............. 435/253.3 |
| 2006/0115861 | A1 | 6/2006 | Shiotsuka et al. ............. 435/7.9 |
| 2006/0275811 | A1 | 12/2006 | Hatakeyama et al. ........... 435/6 |
| 2007/0054315 | A1 | 3/2007 | Imamura et al. .............. 435/7.1 |
| 2007/0178522 | A1 | 8/2007 | Shiotsuka et al. ............ 435/7.1 |
| 2007/0298510 | A1 | 12/2007 | Imamura et al. ............. 436/149 |
| 2008/0000308 | A1 | 1/2008 | Kikuchi et al. ............. 73/866.5 |

FOREIGN PATENT DOCUMENTS

| JP | 2005-312446 | 11/2005 |
| WO | 99/14244 | 3/1999 |
| WO | 2005/095461 | 10/2005 |
| WO | 2007/083793 | 7/2007 |

OTHER PUBLICATIONS

Stephen F. Altschul, et al., "Basic Local Alignment Search Tool", J. Mol. Biol., vol. 215, 1990, pp. 403-410.
Anton Blencowe, et al. "Development and application of diazirines in biological and synthetic macromolecular systems", The Royal Society of Chemistry, Soft Matter, vol. 1, 2005, pp. 178-205.
H. Kaspar Binz, et al., "High-affinity binders selected from designed ankyrin repeat protein libraries", Nature Biotechnology, vol. 22, No. 5, May 2004, pp. 575-582.
Isabelle Caelen, et al., "Protein Density Gradients on Surfaces", Langmuir, vol. 18, 2002, pp. 2463-2467.
Malin Eklund, et al., "Anti-Idiotypic Protein Domains Selected from Protein A-Based Affibody Libraries", Proteins: Structure, Function, and Genetics, vol. 48, 2002, pp. 454-462.

(Continued)

*Primary Examiner*—Shafiqul Haq
(74) *Attorney, Agent, or Firm*—Fitzpatrick, Cella, Harper & Scinto

(57) ABSTRACT

It is intended to provide an anti-photocrosslinking group antibody capable of specifically binding to a photocrosslinking group and available in the binding of a substrate and a substance of interest in a microstructure, a complex protein including at least the antibody or at least a portion thereof, and a technique for use thereof in the detection of a target substance. The present invention provides a protein having at least the structure of an antibody that recognizes a photocrosslinking group.

12 Claims, 10 Drawing Sheets

PUBLICATIONS

G. Galfre, et al., "Antibodies to major histocompatibility antigens produced by hybrid cell lines", Nature, vol. 266, Apr. 7, 1977, pp. 550-552.

Hui Gao, et al., "Photolinker-polymer-mediated immobilization of monoclonal antibodies, F(ab')$_2$ and F(ab') fragments[1]", Biotechnol. Appl. Biochem., vol. 20, 1994, pp. 251-263.

Peter T. Jones, et al., "Replacing the complementarity-determining regions in a human antibody with those from a mouse", Nature, vol. 321, May 29, 1986, pp. 522-525.

Samuel Karlin, et al., "Applications and statistics for multiple high-scoring segments in molecular sequences", Proc. Natl. Acad. Sci., vol. 90, Jun. 1993, pp. 5873-5877.

D. F. Mark, et al., "Site-specific mutagenesis of the human fibroblast interferon gene", Proc. Natl. Acad. Sci., vol. 81, Sep. 1984, pp. 5662-5666.

Sherie L. Morrison, et al., "Chimeric human antibody molecules: Mouse antigen-binding domains with human constant region domains", Proc. Natl. Acad. Sci., vol. 81, Nov. 1984, pp. 6851-6855.

Koh Sato, et al., "Reshaping a Human Antibody to Inhibit the Interleukin 6-dependent Tumor Cell Growth", Cancer Research, vol. 53, Feb. 15, 1993, pp. 851-856.

Hans Sigrist, et al., "Surface immobilization of biomolecules by light", Optical Engineering, vol. 34, No. 8, Aug. 1995, pp. 2339-2348.

Silvia Spinelli, et al., "Lateral Recognition of a Dye Hapten by a Llama VHH Domain", J. Mol. Biol., vol. 311, 2001, pp. 123-129.

Gajendran Sundarababu et al., "Photochemical linkage of Antibodies to Silicon Chips", Photochemistry and Photobiology, vol. 61, No. 6, 1995, pp. 540-544.

http://www.ncbi.nlm.nih.gov.

Official Action dated Oct. 30, 2009 in Korean Application No. 10-2007-0102912.

Hashimoto, et al., "Synthesis of Tag Introducible (3-Trifluoromethyl)phenyldiazirine Based Photoreactive Phenylalanine", Bioorganic & Medicinal Chemistry Letters, vol. 12, 2002, pp. 2507-2510.

* cited by examiner

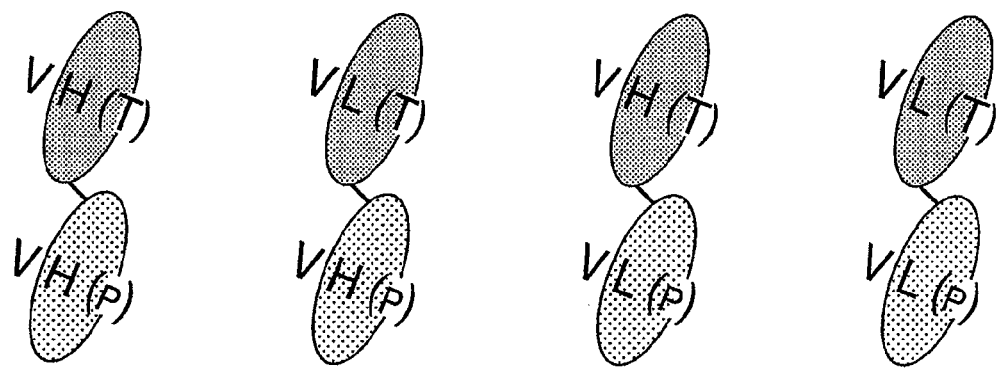
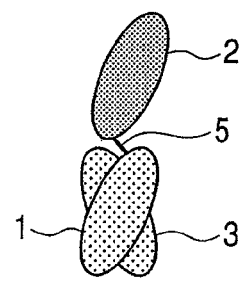
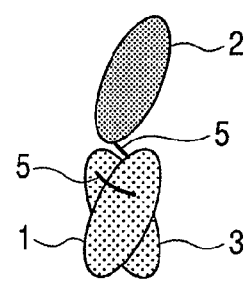
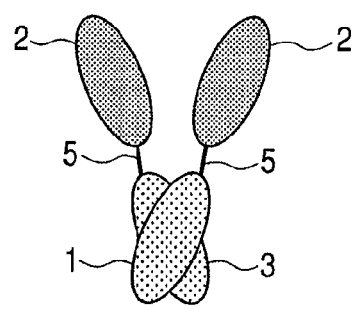

TITRATION CURVE MOUSE No.4/
ANTISERUM-4

TITRATION CURVE MOUSE No.4/
ANTISERUM-5

TITRATION CURVE MOUSE No.5/
ANTISERUM-4

TITRATION CURVE MOUSE No.5/
ANTISERUM-5

TITRATION CURVE 6C9-A5B10 MONOCLONAL ANTIBODY

TITRATION CURVE 6H11-F11F4 MONOCLONAL ANTIBODY

SEQUENCE LISTING

```
<160> NUMBER OF SEQ ID NOS: 24

<210> SEQ ID NO 1
<211> LENGTH: 5
<212> TYPE: PRT
<213> ORGANISM: Mus musculus

<400> SEQUENCE: 1

Ser His Asn Met Leu
1               5

<210> SEQ ID NO 2
<211> LENGTH: 17
<212> TYPE: PRT
<213> ORGANISM: Mus musculus

<400> SEQUENCE: 2

Gly Ile Tyr Pro Gly Asp Gly Asp Thr Ser Tyr Asn Gln Asn Phe Lys
1               5                   10                  15

Gly

<210> SEQ ID NO 3
<211> LENGTH: 8
<212> TYPE: PRT
<213> ORGANISM: Mus musculus

<400> SEQUENCE: 3

Trp Asp Leu Leu Cys Phe Asp Tyr
1               5

<210> SEQ ID NO 4
<211> LENGTH: 5
<212> TYPE: PRT
<213> ORGANISM: Mus musculus

<400> SEQUENCE: 4

Ser Tyr Trp Met His
1               5

<210> SEQ ID NO 5
<211> LENGTH: 15
<212> TYPE: PRT
<213> ORGANISM: Mus musculus

<400> SEQUENCE: 5

Tyr Ile Asn Pro Ser Thr Gly Tyr Thr Glu Tyr Asn Gln Lys Phe
1               5                   10                  15

<210> SEQ ID NO 6
<211> LENGTH: 5
<212> TYPE: PRT
<213> ORGANISM: Mus musculus
```

```
<400> SEQUENCE: 6

Asn Gly Asn Gly Tyr
1               5

<210> SEQ ID NO 7
<211> LENGTH: 10
<212> TYPE: PRT
<213> ORGANISM: Mus musculus

<400> SEQUENCE: 7

Arg Ala Ser Ser Ser Ile Ser Tyr Met His
1               5                   10

<210> SEQ ID NO 8
<211> LENGTH: 6
<212> TYPE: PRT
<213> ORGANISM: Mus musculus

<400> SEQUENCE: 8

Ala Ser Gln Ser Ile Ser
1               5

<210> SEQ ID NO 9
<211> LENGTH: 10
<212> TYPE: PRT
<213> ORGANISM: Mus musculus

<400> SEQUENCE: 9

Gln Gln Trp Ser Asn Ser Pro Pro Tyr Thr
1               5                   10

<210> SEQ ID NO 10
<211> LENGTH: 10
<212> TYPE: PRT
<213> ORGANISM: Mus musculus

<400> SEQUENCE: 10

Thr Ala Ser Gln Ser Ile Ser Tyr Val Val
1               5                   10

<210> SEQ ID NO 11
<211> LENGTH: 7
<212> TYPE: PRT
<213> ORGANISM: Mus musculus

<400> SEQUENCE: 11

Ser Ala Ser Asn Leu Ala Ser
1               5

<210> SEQ ID NO 12
<211> LENGTH: 8
<212> TYPE: PRT
<213> ORGANISM: Mus musculus

<400> SEQUENCE: 12

Gly Gln Gly Tyr Ser Pro Leu Thr
1               5

<210> SEQ ID NO 13
<211> LENGTH: 117
<212> TYPE: PRT
<213> ORGANISM: Mus musculus

<400> SEQUENCE: 13
```

Gln Val Lys Leu Gln Glu Ser Gly Ala Glu Leu Val Lys Pro Gly Ala
1               5                   10                  15

Ser Val Arg Met Ser Cys Lys Ala Ser Gly Tyr Thr Phe Thr Ser His
            20                  25                  30

Asn Met Leu Trp Ile Lys Gln Thr Pro Gly Gln Gly Leu Lys Trp Ile
            35                  40                  45

Gly Gly Ile Tyr Pro Gly Asp Gly Asp Thr Ser Tyr Asn Gln Asn Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Trp Asp Leu Leu Cys Phe Asp Tyr Trp Gly Gln Gly Thr Thr
                100                 105                 110

Val Thr Val Ser Ser
            115

<210> SEQ ID NO 14
<211> LENGTH: 107
<212> TYPE: PRT
<213> ORGANISM: Mus musculus

<400> SEQUENCE: 14

Gln Ile Val Leu Thr Gln Ser Pro Ala Thr Leu Ser Val Thr Pro Gly
1               5                   10                  15

Asn Lys Val Thr Leu Thr Cys Arg Ala Ser Ser Ser Ile Ser Tyr Met
            20                  25                  30

His Trp Tyr Gln Gln Lys Pro Gly Gln Ser Pro Arg Leu Leu Ile Lys
            35                  40                  45

Tyr Ala Ser Gln Ser Ile Ser Gly Val Pro Ser Arg Phe Ser Gly Ser
50                  55                  60

Gly Ser Gly Thr Asp Phe Thr Leu Thr Ile Thr Ser Val Glu Ala Glu
65                  70                  75                  80

Asp Thr Ala Thr Tyr Tyr Cys Gln Gln Trp Ser Asn Ser Pro Pro Tyr
                85                  90                  95

Thr Phe Gly Gly Gly Thr Lys Leu Glu Leu Lys
                100                 105

<210> SEQ ID NO 15
<211> LENGTH: 114
<212> TYPE: PRT
<213> ORGANISM: Mus musculus

<400> SEQUENCE: 15

Gln Val Gln Leu Gln Glu Leu Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Tyr Ile Asn Pro Ser Thr Gly Tyr Thr Glu Tyr Asn Gln Lys Phe
50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Gly Asn Gly Tyr Trp Gly Gln Gly Thr Thr Val Thr Val
            100                 105                 110

Ser Ser

<210> SEQ ID NO 16
<211> LENGTH: 105
<212> TYPE: PRT
<213> ORGANISM: Mus musculus

<400> SEQUENCE: 16

Asp Ile Val Leu Thr Gln Ser Pro Ser Ser Leu Ser Val Thr Pro Gly
1               5                   10                  15

Glu Lys Val Thr Leu Thr Cys Thr Ala Ser Gln Ser Ile Ser Tyr Val
            20                  25                  30

Val Trp Tyr Gln Gln Lys Pro Gly Gln Ser Pro Lys Leu Leu Ile Tyr
        35                  40                  45

Ser Ala Ser Asn Leu Ala Ser Gly Val Pro Asp Arg Phe Ser Gly Ser
    50                  55                  60

Gly Ser Gly Thr Asp Phe Ser Leu Thr Ile Ser Ser Val Glu Ala Glu
65                  70                  75                  80

Asp Leu Ala Val Tyr Phe Cys Gly Gln Gly Tyr Ser Pro Leu Thr Phe
                85                  90                  95

Gly Ser Gly Thr Lys Leu Glu Leu Lys
            100                 105

<210> SEQ ID NO 17
<211> LENGTH: 36
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (1)..(5)
<223> OTHER INFORMATION: n is a, c, g, or t

<400> SEQUENCE: 17
nnnnnccatg gcccaggtgc agctgcagga gctggg                              36

<210> SEQ ID NO 18
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (1)..(5)
<223> OTHER INFORMATION: n is a, c, g, or t

<400> SEQUENCE: 18
nnnnngctag ctgaggagac ggtgaccgtg g                                   31

<210> SEQ ID NO 19
<211> LENGTH: 47
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (1)..(5)
<223> OTHER INFORMATION: n is a, c, g, or t

<400> SEQUENCE: 19

```
nnnnngctag cggtggcggt ggctctgata tcgtcctgac ccagagc                    47

<210> SEQ ID NO 20
<211> LENGTH: 32
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (1)..(5)
<223> OTHER INFORMATION: n is a, c, g, or t

<400> SEQUENCE: 20
nnnnnccgcg gatttcagct ccagcttggt cc                                   32

<210> SEQ ID NO 21
<211> LENGTH: 352
<212> TYPE: DNA
<213> ORGANISM: Mus musculus

<400> SEQUENCE: 21
caggtgaagc tgcaggagtc aggggctgag ctggtgaagc ctggggcctc agtgaggatg     60
tcctgtaagg cttctggcta cacatttacc agtcacaata tgctctggat aaaacagaca    120
cctggacagg gcctgaaatg gattggaggt atttatccag agatggtgaa tacttcctac    180
aatcagaact tcaaaggcaa ggccacattg actgcagaca aatcctccag tacagcctac    240
atgcagctca gcagcctgac atctgaggac tctgcggtct atttctgtgc aagatgggat    300
ctactttgtt ttgactattg gggccaaggg accacggtca ccgtctcctc aa            352

<210> SEQ ID NO 22
<211> LENGTH: 322
<212> TYPE: DNA
<213> ORGANISM: Mus musculus

<400> SEQUENCE: 22
cagatcgtcc tgacccagag cccggcgacc ctctcggtca ccccggcaa caaggtgacc      60 ctcacctgcc gcgcctcgtc gtcgatctcg tacatgcact ggtatcagca gaagccgggg    120
cagagcccgc gcctcctgat caagtacgcc agccagtcga tctcgggggt gccgtcgcgc    180
ttcagcggct cgggctcggg caccgacttc accctgacga tcaccagcgt cgaggccgag    240
gacaccgcca cctactactg ccagcagtgg tcgaacagcc gccgtacac cttcggcggc     300 gggaccaagc tggagctgaa ac                                            322

<210> SEQ ID NO 23
<211> LENGTH: 343
<212> TYPE: DNA
<213> ORGANISM: Mus musculus

<400> SEQUENCE: 23
caggtgcagc tgcaggagct gggggctgaa ctggcaaaac ctggggcctc agtgaagatg     60
tcctgcaagg cttctggcta cacctttact agctactgga tgcactgggt aaaacagagg    120
cctggacagg gtctggaatg gattggatac attaatccta gcactggtta tactgagtac    180
aatcagaagt tcaaggacaa ggccacattg actgcagaca aatcctccag cacagcctac    240
atgcaactga gcagcctgac atctgaggac tctgcagtct attactgtgc aagaaatggt    300
aatgggtact ggggccaagg gaccacggtc accgtctcct caa                      343
```

-continued

```
<210> SEQ ID NO 24
<211> LENGTH: 316
<212> TYPE: DNA
<213> ORGANISM: Mus musculus

<400> SEQUENCE: 24
gatatcgtcc tgacccagag cccgtcgtcg ctctcggtca cccccggcga gaaggtgacc      60
ctcacctgca ccgcctcgca gtcgatctcg tacgtggtgt ggtatcagca gaagccgggg     120
cagagcccga agctcctgat ctactcggcc agcaacctcg cctcgggggt gccggaccgc     180
ttcagcggct cgggctcggg caccgacttc tcgctgacga tctcgagcgt cgaggccgag     240
gacctcgccg tgtacttctg cgggcagggg tacagcccgc tcaccttcgg cagcgggacc     300
aagctggagc tgaaac                                                    316
```

PROTEIN, METHOD FOR IMMOBILIZING PROTEIN, STRUCTURE, BIOSENSOR, NUCLEIC ACID, VECTOR AND KIT FOR DETECTING TARGET SUBSTANCE

BACKGROUND OF THE INVENTION

1. Field of the Invention

The present invention relates to a protein, a method for immobilizing the protein onto a substrate, a structure including a protein and a substrate, a biosensor including the structure, a nucleic acid encoding the protein, a vector including the nucleic acid, and a kit for detecting a target substance, including the substrate and the protein.

2. Description of the Related Art

Biomolecules typified by nucleic acids and proteins have been known to constitute precise structure. This precise structure is controlled at the atomic level for exerting the functions of the biomolecules. Studies have been made to provide the biomolecules onto a variety of materials by use of such properties of the biomolecules. These techniques have been utilized mainly in fields including biosensors, biomolecule purification processes, and further, the utilization of biomolecules in nanoscale structure formation in semiconductor processes in recent years. For example, Japanese Patent Application Laid-Open No. 2005-312446 discloses a gold-binding protein capable of specifically binding to gold and available in the binding of gold and a substance of interest (target substance). The protein disclosed therein includes at least a portion of an antibody having binding properties to gold. This protein has antibody structure serving as a scaffold and directly recognizes gold based on the antigen recognition ability of the antibody. In Japanese Patent Application Laid-Open No. 2005-312446, this protein is intended to be applied to a biosensor using a gold substrate. Moreover, in Japanese Patent Application Laid-Open No. 2005-312446, the protein is immobilized through molecular recognition toward gold. Therefore, orientation is imparted to the immobilized protein so as to homogeneously immobilize the protein. As a result, improvement in the performance of the biosensor is expected.

However, in Japanese Patent Application Laid-Open No. 2005-312446, molecular recognition, which is seen in antigen-antibody reaction, is utilized in the immobilization of the proteins onto the gold substrate. Therefore, the proteins are noncovalently immobilized thereon. Thus, not a few immobilized proteins might be dissociated. As a result, kinetic analysis is required for biosensor use. Alternatively, application of this protein, when used in a biosensor, is limited to biosensors using a gold substrate. Therefore, a technique for preventing non-specific adsorption to the gold substrate must be devised.

Meanwhile, studies have heretofore been made on a method for immobilizing a protein onto a substrate by use of the physical adsorption or chemical crosslinking of proteins. Alternatively, the production of a biosensor for detecting a variety of target substances usually requires the number of immobilized proteins equal to or more than the number of target substances to be detected. Therefore, an approach for efficiently immobilizing these proteins by a single method is demanded. However, basically, the immobilized proteins are chemically diverse. These immobilized proteins differ in the types and amounts of functional groups and also in the positions of functional groups on the protein surfaces. As a result, it was often very difficult to homogeneously immobilize plural proteins onto a substrate by the same immobilization method.

On the other hand, Langmuir (2002) 18, 2463-2467 discloses a technique for covalently immobilizing proteins onto a substrate via photocrosslinking groups. In this technique, a non-specific adsorption-preventing polymer having photo-crosslinking groups is utilized. Therefore, the difference in functional groups depending on protein types is almost negligible. Thus, proteins can be immobilized more homogeneously by this technique than by conventional immobilization. However, Langmuir (2002) 18, 2463-2467 merely suggests that variations in the amounts of proteins immobilized depending on their types are reduced. Langmuir (2002) 18, 2463-2467 avoids any mention of immobilization having the homogeneous orientation of proteins required for biosensors.

Another widely known immobilization method includes introducing a particular sequence (e.g., His Tag or Cysteine residue) into the ends or particular sites of proteins to be immobilized so as to impart enhanced orientation to the proteins thus modified. However, such protein modification might adversely affect the productivity of a certain protein in microorganisms or might reduce the target substance capture activity of the proteins due to the influence of the substrate surface attributed to the low molecular weight of the introduced residue.

The proteins of Japanese Patent Application Laid-Open No. 2005-312446 are immobilized onto a gold substrate through molecular recognition reaction. Therefore, a very homogeneous immobilized state excellent in orientation can be obtained. However, this immobilization, which utilizes only the molecular recognition reaction, is noncovalent on the obtained structure. Therefore, the proteins might be dissociated from the substrate with a certain probability. Thus, Japanese Patent Application Laid-Open No. 2005-312446 provides homogeneous immobilization and, however, does not disclose a method for covalently immobilizing proteins. Moreover, Japanese Patent Application Laid-Open No. 2005-312446 does not disclose a method for immobilizing proteins onto substrates other than the gold substrate by use of molecular recognition reaction.

On the other hand, Langmuir (2002) 18, 2463-2467 discloses the covalent immobilization of proteins via photocrosslinking groups. According to the method of Langmuir (2002) 18, 2463-2467, the difference in functional groups of a variety of proteins is substantially negligible. Thus, proteins can be immobilized homogeneously to some extent onto a substrate. However, Langmuir (2002) 18, 2463-2467 does not disclose an immobilization method capable of imparting orientation to proteins.

Meanwhile, considering the production process, cost and performance of a variety of instruments such as biosensors or diagnostic devices at the commercial level, it is demanded to obtain functions of interest such as sensitivity by use of smaller amounts of capture proteins. It is also demanded to reduce the number of production processes or production time of these instruments. Thus, it is important to efficiently immobilize, in a short time, smaller amounts of proteins with high binding activity to target substances onto a substrate. Alternatively, such a protein immobilization technique is used to produce commercially available, capture protein-mounted medical instruments such as biosensors, diagnostic drugs or diagnostic devices. In this case, it is important to immobilize proteins with more accurate orientation onto a substrate in terms of reproducibility and precision. Protein productivity contributes to the cost reduction of devices. Therefore, it is demanded to produce capture proteins in large amounts in microorganisms.

An object of the present invention is to expand the possibility of providing a technique for satisfying the requirements both for capture proteins and for protein immobilization techniques. Another object of the present invention is to provide a protein capable of crosslinking to a substrate surface through light irradiation. Specifically, this protein can be produced stably even by genetic engineering production in microorganisms and can be immobilized covalently with good orientation onto a substrate.

SUMMARY OF THE INVENTION

The present invention provides a protein including an antibody that recognizes at least a photocrosslinking group including a reactive phenyldiazirine derivative represented by the following General Formula 1:

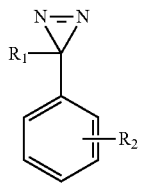

(wherein $R_1$ represents one selected from the group consisting of a hydrogen atom and an alkyl group which may have a substituent, and $R_2$ represents one selected from the group consisting of a hydrogen atom, a halogen atom, an alkoxy group and an alkyl group which may be substituted by alkylene oxide).

The protein of the present invention may include an antibody that recognizes only the photocrosslinking group or may include an antibody that recognizes the photocrosslinking group in combination with other portions.

Examples of the antibody include those produced by hybridomas deposited as accession Nos. FERM P-20855 (FERM BP-10762 (transferred to international deposit)), FERM P-20856 (FERM BP-10763 (transferred to international deposit)), FERM P-20857 (FERM BP-10764 (transferred to international deposit)), FERM BP-10825 (internationally deposited de novo) and FERM BP-10826 (internationally deposited de novo).

Alternatively, examples of the antibody include those having complementarity-determining regions including amino acid sequences of any of the following (a) to (d) or complementarity-determining regions functionally equivalent thereto: (a) amino acid sequences including sequences of SEQ ID NOs: 1, 2 and 3; (b) amino acid sequences including sequences of SEQ ID NOs: 4, 5 and 6; (c) amino acid sequences including sequences of SEQ ID NOs: 7, 8 and 9; and (d) amino acid sequences including sequences of SEQ ID NOs: 10, 11 and 12.

Alternatively, examples of the antibody include those selected from the group consisting of a chimeric antibody, a complementarity-determining region-grafted antibody, a single-chain antibody and antibody fragments thereof.

The present invention also provides a protein capable of binding to a target substance, including at least one first region that recognizes a photocrosslinking group including a reactive phenyldiazirine derivative, and at least one second region that recognizes the target substance, wherein the first region includes any of the proteins described above or a portion thereof, and the target substance recognized by the second region is different from the photocrosslinking group including a reactive phenyldiazirine derivative.

The present invention also provides a method for immobilizing a protein onto a substrate by use of the ability of the protein to recognize a crosslinking group and crosslinking reaction, including the steps of 1) providing a substrate surface with a photocrosslinking group including a reactive phenyldiazirine derivative as a crosslinking group, 2) reacting any of the proteins described above with the crosslinking group on the substrate surface by use of the ability of the protein to recognize the crosslinking group so as to immobilize the protein onto the substrate, and 3) irradiating the substrate with light after or simultaneously with the reaction so as to form crosslinking structure between the substrate and the protein through photocrosslinking reaction using the photocrosslinking group.

The present invention also provides a structure including a substrate and a protein, wherein the substrate has a reactive phenyldiazirine derivative as a crosslinking group on at least a portion of the surface, and the protein is any of the proteins described above.

The present invention also provides a biosensor including the structure.

The present invention also provides a nucleic acid encoding any of the proteins described above.

The present invention also provides a vector including the nucleic acid.

The present invention also provides a kit for detecting a target substance, including a substrate and a protein for forming the structure.

Further features of the present invention will become apparent from the following description of exemplary embodiments with reference to the attached drawings.

BRIEF DESCRIPTION OF THE DRAWINGS

FIGS. 1A, 1B, 1C and 1D are respectively a diagram schematically illustrating the constitution of a structure according to one example of a complex protein of the present invention.

FIGS. 2A and 2B are respectively a diagram schematically illustrating the constitution of a structure according to one example of a complex protein of the present invention.

FIG. 3 is a diagram schematically illustrating the constitution of a structure according to one example of a complex protein of the present invention.

DESCRIPTION OF THE EMBODIMENTS

Figure 4A:
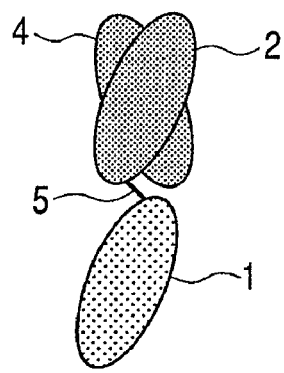
FIGS. 4A and 4B are respectively a diagram schematically illustrating the constitution of a structure according to one example of a complex protein of the present invention.

A protein of the present invention includes an antibody that recognizes at least a photocrosslinking group including a reactive phenyldiazirine derivative. The protein of the present invention may be a protein that recognizes only the photocrosslinking group including a reactive phenyldiazirine derivative or may be a protein that recognizes a site including the photocrosslinking group (the photocrosslinking group and the neighborhood thereof). The former is a "protein including an antibody that recognizes only a photocrosslinking group including a reactive phenyldiazirine derivative". Specifically, this protein includes an antibody that recognizes the photocrosslinking group in itself. The latter is a protein including an "antibody that recognizes at least a photocrosslinking group including a reactive phenyldiazirine derivative". In this case, the antibody also recognizes portions other than the photocrosslinking group.

This antibody that recognizes a photocrosslinking group is used as at least a portion of a protein having desired functions. Furthermore, this photocrosslinking group is provided on a substrate surface. As a result, the favorable immobilized state of this protein onto the substrate surface can be obtained by use of molecular recognition. Moreover, the favorable covalently immobilized state of the protein can be obtained through light irradiation.

This antibody that recognizes a photocrosslinking group, which is available in the present invention, is produced by the following hybridomas deposited with International Patent Organism Depositary, National Institute of Advanced Industrial Science and Technology as accession Nos. FERM P-20855 (FERM BP-10762 (transferred to international deposit)), FERM P-20856 (FERM BP-10763 (transferred to international deposit)), FERM P-20857 (FERM BP-10764 (transferred to international deposit)), FERM BP-10825 (internationally deposited de novo) and FERM BP-10826 (internationally deposited de novo): Mouse-Mouse hybridoma 1E2-2H6-1A9 (FERM P-20855): Date of accession: Mar. 29, 2006, (FERM BP-10762): transferred to international deposit on Jan. 19, 2007; Mouse-Mouse hybridoma 6A8-1C6-1B6 (FERM P-20856): Date of accession: Mar. 29, 2006, (FERM BP-10763): transferred to international deposit on Jan. 19, 2007; Mouse-Mouse hybridoma 6C9-A5B10 (FERM P-20857): Date of accession: Mar. 29, 2006, (FERM BP-10764): transferred to international deposit on Jan. 19, 2007; Mouse-Mouse hybridoma 4G2-1E10-1F10 (FERM BP-10825): Date of accession: May 10, 2007; and Mouse-Mouse hybridoma 6H11-F11F4 (FERM BP-10826): Date of accession: May 10, 2007.

Further examples of this antibody can include an antibody having complementarity-determining regions including amino acid sequences of any of the following (a) to (d) or complementarity-determining regions functionally equivalent thereto: (a) amino acid sequences including sequences of SEQ ID NOs: 1, 2 and 3; (b) amino acid sequences including sequences of SEQ ID NOs: 4, 5 and 6; (c) amino acid sequences including sequences of SEQ ID NOs: 7, 8 and 9; and (d) amino acid sequences including sequences of SEQ ID NOs: 10, 11 and 12.

In this context, the "complementarity-determining regions functionally equivalent" refer to these amino acid sequences that maintain the ability to recognize the photocrosslinking group, even when modified by amino acid deletion, substitution or insertion. Examples thereof can include the amino acid sequences modified by the deletion, substitution or insertion of one or several amino acids within the range that maintains the ability to recognize the photocrosslinking group.

The antibody can have any form selected from the group consisting of a chimeric antibody, a complementarity-determining region-grafted antibody, a single-chain antibody and antibody fragments thereof.

The antibody can be used to obtain a protein capable of binding to a target substance. Specifically, this protein includes the following constitutions: (1) at least one first region that recognizes a photocrosslinking group including a reactive phenyldiazirine derivative, (2) at least one second region that recognizes a substance different from that recognized by the first region, and (3) wherein the first region includes the protein including the antibody or a portion thereof.

The target substance recognized by the second region varies depending on the desired functions of the protein appropriate to the application of this structure. For example, the target substance is a substance to be detected in a biosensor or a substance to be separated in a separation process. This second region may be provided at two or more positions. In this case, these two or more different second regions can recognize two or more different target substances.

The present invention can further provide a method for immobilizing the protein including an antibody that recognizes at least a photocrosslinking group or the protein capable of binding to a target substance onto a substrate by use of the ability of the protein to recognize a photocrosslinking group and crosslinking reaction. This immobilization method includes the steps of 1) providing a substrate surface with a reactive phenyldiazirine derivative as a crosslinking group, 2) reacting the protein including an antibody that recognizes at least a photocrosslinking group including a reactive phenyldiazirine derivative with the crosslinking group on the substrate surface by use of the ability of the protein to recognize the crosslinking group so as to immobilize the protein onto the substrate, and 3) irradiating the substrate with light after or simultaneously with the reaction so as to form crosslinking structure between the substrate and the protein through photocrosslinking reaction using the photocrosslinking group.

The protein including an antibody that recognizes at least a photocrosslinking group or the protein capable of binding to a target substance can be immobilized onto a substrate to obtain a structure that can be expected to be utilized in a variety of fields such as biosensors and biomolecule purification processes. An enzyme having functions for biosensor use or a protein for capturing a substance to be detected is used as a protein constituting this structure. In this case, this structure is available as a sensor portion of a biosensor. Furthermore, at least a protein and a substrate for forming this structure can be used to constitute a kit for detecting a target substance to be detected.

On the other hand, a nucleic acid encoding the protein including an antibody that recognizes at least a photocrosslinking group or the protein capable of binding to a target substance is incorporated into a vector and expressed in host cells such as microorganisms. As a result, these proteins can be produced stably.

The protein having the ability to recognize a photocrosslinking group according to the present invention has a photocrosslinking group-binding site and a structural part. As a result, the immobilization of a target substance-binding site, which is linked to this structural part, onto a substrate surface has no or very little influence on the original functions of the target substance-binding site. The distance is kept between the target substance-binding site and the substrate by the presence of the structural part. Therefore, the target substance-binding site does not undergo interaction from the substrate that has an influence on its functions. As a result, the protein can possess the high ability to capture a target substance.

When the protein having the ability to recognize a photocrosslinking group according to the present invention is used in a biosensor, a detection method is not limited basically. Any detection method is available. Thus, any method can be used without particular limitations as long as the structure can maintain the immobilized state using the photocrosslinking group. Specifically, the protein having the ability to recognize a photocrosslinking group according to the present invention can be immobilized by crosslinking onto a substrate surface through light irradiation. This protein, when used in a biosensor, can be immobilized covalently and oriented very stably and homogeneously, leading to improvement in the precision of the biosensor.

Figure 12:
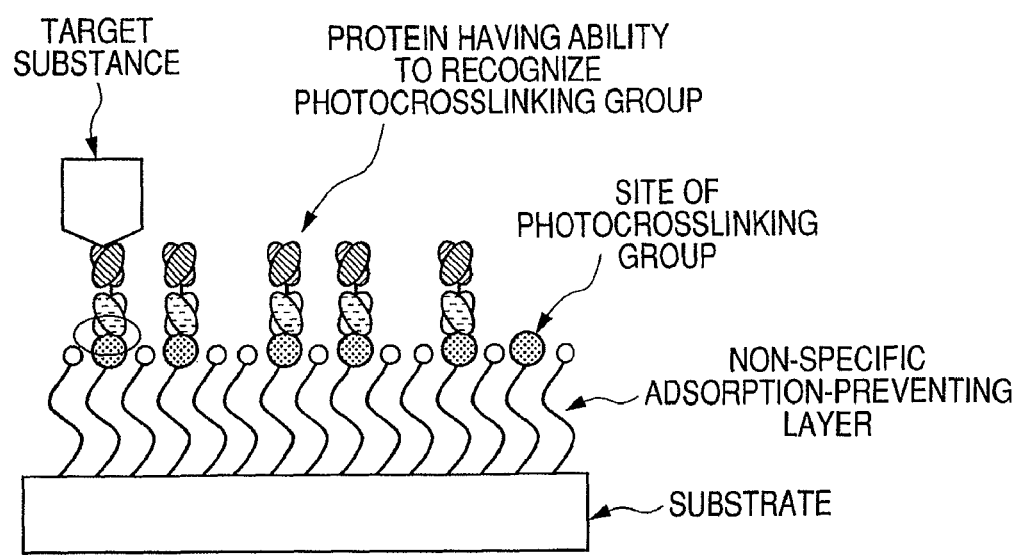
FIG. 12 is a diagram schematically illustrating the construction of one example of a biosensor to which a structure of the present invention is applicable.

FIG. 12 illustrates the construction of one example of a biosensor to which the structure of the present invention is applicable. First, a non-specific adsorption-preventing layer including a protein having the effect of preventing non-specific adsorption is provided on a substrate of this biosensor. A photocrosslinking group-recognizing complex protein having target substance capture functions is immobilized by use of a photocrosslinking group provided on the surface of this non-specific adsorption-preventing layer. A target substance is sensed based on the presence or absence of the target substance captured by this photocrosslinking group-recognizing complex protein.

Furthermore, a protein having the ability to recognize a photocrosslinking group and further having the ability to recognize a target substance, that is, further having specific binding properties to a target substance (hereinafter, referred to as a photocrosslinking group-recognizing complex protein) according to the present invention can be used to form a multilayer body including at least the following factors (i) to (iii): (i) a substrate having a photocrosslinking group on at least a portion of the surface; (ii) the photocrosslinking group-recognizing complex protein of the present invention; and (iii) a target substance that can be bound by the photocrosslinking group-recognizing complex protein of the present invention.

A photocrosslinking group-recognizing complex protein that recognizes two or more different target substances can also be used. In this case, the photocrosslinking group-recognizing complex protein can have at least an immunoglobulin structure with a sterically stabilized beta-sheet as a photocrosslinking group-recognizing site. As a result, the spatial position can be kept between the substrate and the target substance-binding site. Specifically, the target substance-binding site of the photocrosslinking group-recognizing complex protein does not undergo some interaction from the substrate including a photocrosslinking group and can maintain the ability to bind to a target substance. This also allows for the formation of a very thin, accurately oriented multilayer structure. A detection apparatus can be constituted by use of these properties of this photocrosslinking group-recognizing complex protein. For example, a sensing device for desired target substance(s) can be produced by providing a molecular layer having at least a photocrosslinking group onto a thin gold film and further providing thereonto a photocrosslinking group-recognizing complex protein capable of binding to one or more desired target substance(s). In this case, an optical unit, for example, a unit using surface plasmon resonance, can be utilized as a method for detecting the target substance captured by the photocrosslinking group-recognizing complex protein.

When the protein having the ability to recognize a photocrosslinking group according to the present invention is immobilized on a substrate, the amount of the protein immobilized can be controlled at a desired level in a short time by changing a light irradiation dose and the timing of irradiation. This approach can be expected to have advantages at the commercial level such as reduction in the number of production processes of a biosensor and reduction in the amount of the protein used.

Hereinafter, the protein having the ability to recognize a photocrosslinking group according to the present invention, a structure using this protein, and use thereof in the detection of a target substance will be described more specifically.

(1) Protein Having Ability to Recognize Photocrosslinking Group

Photocrosslinking Group

The protein having the ability to recognize a photocrosslinking group according to the present invention includes an anti-photocrosslinking group antibody that recognizes at least a photocrosslinking group. The photocrosslinking group recognized by this antibody is a reactive phenyldiazirine derivative provided at a predetermined site of a substrate without impairing its functions. This reactive phenyldiazirine derivative is represented by the following General Formula 1:

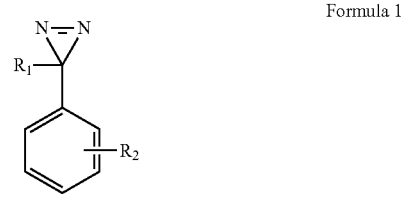

Formula 1

(wherein $R_1$ represents one selected from the group consisting of a hydrogen atom and an alkyl group which may have a substituent, and $R_2$ represents one selected from the group consisting of a hydrogen atom, a halogen atom, an alkoxy group and an alkyl group which may be substituted by alkylene oxide).

$R_1$ is selected from the group consisting of a hydrogen atom and an alkyl group which may be substituted. The substituent of the alkyl group of $R_1$ can be an electron-withdrawing group such as a fluorine atom, particularly, a trifluoromethyl group.

$R_2$ is selected from the group consisting of a hydrogen atom, a halogen atom, an alkoxy group and an alkyl group which may be substituted by alkylene oxide. $R_2$ can represent one selected from the group consisting of a hydrogen atom and an alkoxy group. This alkoxy group can have 1 to 3 carbon atoms. The alkyl group which may be substituted by alkylene oxide can be represented by the formula $-(C_mH_{2m}O)_n-(CH_2)_o-R_4$, wherein m represents any integer of 2 and 3, n represents any integer of 1 to 6, o represents any integer of 1 to 4, and $R_4$ represents one selected from the group consisting of a hydrogen atom, a carboxyl group, an amino group and a hydroxyl group and can represent a hydrogen atom. For example, a polyethylene glycol chain can be utilized as alkylene oxide in terms of the stabilization of the immobilized protein. Alternatively, $R_2$ can take a meta position to —CN$_2$R$_1$. The diazirine compound may have plural R$_2$ moieties which may be identical or different as long as the photocrosslinking group-recognizing protein can recognize the compound. These plural R$_2$ moieties can also take a meta position to —CN$_2$R$_1$.

The group including the reactive phenyldiazirine derivative, when provided onto a substrate surface, has structure represented by the following General Formula 2:

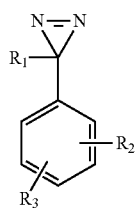

Formula 2

R$_3$ represents a functional group for holding and immobilizing the photocrosslinking group onto a substrate. R$_3$ may be any group that can be reactive with a functional group held on the substrate surface and is selected from, for example, a carboxyl group, a formyl group, an active ester group, a hydroxyl group, thiol, sulfide, an amino group, a halogen-substituted alkyl group, a trialkoxysilyl group and groups having substituents thereof. R$_3$ can take a para position to —CN$_2$R$_1$.

A conjugate is prepared between a protein having the effect of preventing non-specific adsorption and a compound supplying a photocrosslinking group, for the purpose of preventing the non-specific adsorption of a target substance onto a substrate. This conjugate can be used as a molecule having a photocrosslinking group. For example, a conjugate can be produced with BSA (Bovine Serum Albumin) or a casein protein. In this case, a photocrosslinking group can be linked via R$_3$ to the protein such as BSA or a casein protein. These conjugates can be utilized to simultaneously perform a treatment for preventing non-specific adsorption to a predetermined site on a substrate surface and a treatment for immobilizing a capture protein onto the substrate, for example, in a biosensor. Alternatively, a conjugate may be produced between a protein used at an immunization step for creating an anti-photocrosslinking group antibody and a carrier protein, for example, OVA (Ovalbumin) or KLH (Keyhole Limpet Haemocyanin). Any molecule having a photocrosslinking group may be used as long as the ability to recognize a photocrosslinking group characteristic of the present protein can be exerted.

Photocrosslinking is achieved by UV irradiation around 350 nm. The orientational immobilization of the protein through photocrosslinking according to the present invention can be confirmed by mass spectrometry such as TOF mass. Specifically, the protein of the present invention recognizes a photocrosslinking group through molecular recognition and is further crosslinked through light irradiation. Therefore, the photocrosslinking of a particular region can be confirmed by treating the structure of the present invention with an appropriate protease and subjecting the decomposition product to mass spectrometry.

Molecular Recognition

The protein of the present invention has at least the ability to recognize a photocrosslinking group as a molecular recognition ability. Molecular recognition encompasses antigen-antibody reaction as biomolecular reaction. The dissociation constant K$_D$ value of the conjugate thereof can be 10$^{-4}$ M or less. When the K$_D$ value is 10$^{-4}$ M or less, the adsorption behavior of a non-specifically adsorbed protein can be distinguished sufficiently from the molecular recognition, for example, by a biomolecular interaction measurement apparatus such as calorimetry, SPR or QCM. The dissociation constant can be 10$^{-6}$ M or less from the viewpoint of reduction in the operation time of protein immobilization.

Antibody

The anti-photocrosslinking group antibody used in the present invention can be formed with the whole anti-photocrosslinking group antibody or with a portion including the crosslinking group-recognizing site. This anti-photocrosslinking group antibody is used in binding with a photocrosslinking group (or a derivative thereof) or a site including at least a photocrosslinking group (or a derivative thereof). Such an antibody that can be used may be an antibody produced by lymphoid cells of every vertebrate animal or may be an antibody (variant antibody) having an amino acid sequence derived from the amino acid sequence thereof with the deletion, substitution or addition of one or several amino acids and maintaining the structure and functions of the original antibody. Antibodies are classified into IgG, IgM, IgA, IgD and IgE in the (immunological or physical) classification of their characteristics. The antibody used in the present invention may belong to any of the classes. Furthermore, these antibodies may form a multimer. For example, IgA and IgM form a dimer and a pentamer, respectively. These multimers can be used without problems as long as their forms are capable of binding to a photocrosslinking group. The antibody, when used in vitro, is not limited to mammalian antibodies and may be IgW or IgY.

The antibody of the present invention particularly encompasses a "chimeric" antibody. This chimeric antibody has a portion of heavy (H) and/or light (L) chains derived from a particular species or from a particular antibody class or subclass and the remaining portion of the chain derived from another species or from another antibody class or subclass. The antibody of the present invention further encompasses the variant antibody described above and antibody fragments. These antibodies have been disclosed in U.S. Pat. No. 4,816, 567; Morrison et al., Proc. Natl. Acad. Sci. USA 81: 6851-6855 (1984).

In the present invention, the "variant antibody" refers to an amino acid sequence variant of the antibody having one or more modified amino acid residue(s). For example, the variable region of the antibody can be modified for improving the ability to bind to a photocrosslinking group. Such modification can be performed by methods such as site-specific mutagenesis, PCR mutagenesis and cassette mutagenesis. Such a variant has at least 70% identity to the amino acid sequence of the heavy or light chain variable region of the antibody and can have at least 90% identity, particularly, at least 95% identity thereto. The sequence identity is defined herein as a percentage of residues identical to residues in the amino acid sequence of the original antibody after sequence alignment as appropriate for the highest sequence identity and the appropriate introduction of a gap.

Complementarity-determining regions functionally equivalent to the complementarity-determining regions (CDRs) of the antibody of the present invention refer to those having amino acid sequences similar to the CDR amino acid sequences of the antibody of the present invention and binding to at least a photocrosslinking group through molecular recognition. This CDR region exists in the variable region of the antibody and determines antigen-binding specificity. Three CDRs are present in each of H and L chains and are designated as CDR1, CDR2 and CDR3 in this order from the N-terminal side. The CDRs are interposed between four regions having a highly conserved amino acid sequence. These four regions are called frameworks. The CDRs may be grafted to other antibodies. A recombinant antibody can be produced by combining the CDRs with the frameworks of a desired antibody. Alternatively, one or several CDR amino acids may be modified with the binding properties to an antigen maintained. For example, one or several CDR amino acids can be substituted, deleted and/or added.

For inducing a variation by amino acid residue substitution, it is desired that the amino acid residue should be substituted by another amino acid in which the properties of the side chain in the amino acid are conserved. For example, the properties of the side chain in the amino acid can be classified as follows: (1) hydrophobic amino acids (A, I, L, M, F, P, W, Y and V); (2) hydrophilic amino acids (R, D, N, C, E, Q, G, H, K, S and T); (3) amino acids having an aliphatic side chain (G, A, V, L, I and P); (4) amino acids having a hydroxyl group-containing side chain (S, T and Y); (5) amino acids having a sulfur atom-containing side chain (C and M); (6) amino acids having a carboxylic acid- and amide-containing side chain (D, N, E and Q); (7) amino acids having a base-containing side chain (R, K and H); and (8) amino acids having an aromatic group-containing side chain (H, F, Y and W).

Amino acid substitution within each of these groups is referred to as conservative substitution. It has already been known that a polypeptide having a certain amino acid sequence modified by the deletion and/or addition of one or several amino acid residues therein and/or by substitution by other amino acids maintains its biological activity. This point has been disclosed in Mark, D. F. et al., Proc. Natl. Acad. Sci. USA (1984) 81, 5662-5666. The number of amino acids varied is not particularly limited. In general, 40% or less of amino acids in each CDR is varied. Alternatively, 35% or less of the amino acids, particularly, 30% or less of the amino acids, can be varied. Amino acid sequence identity may be determined as described herein.

Specifically, nucleotide sequence and amino acid sequence identities can be determined by the algorithm BLAST of Karlin and Altschul (Proc. Natl. Acad. Sci. USA 90: 5873-5877, 1993). Based on this algorithm, programs called BLASTN and BLASTX have been developed. This point has been disclosed in Altschul et al. J. Mol. Biol. 215: 403-410, 1990. The specific approaches of these analysis methods are known in the art. In this regard, the website of BLAST (Basic Local Alignment Search Tool) in NCBI (National Center for Biotechnology Information) (http://www.ncbi.nlm.nih.gov) can be referred to.

Chimeric antibody, complementarity-determining region (CDR)-grafted antibody and antibody fragment In the present invention, artificially modified, genetically recombinant antibodies, for example, chimeric and humanized antibodies can be used for the purpose of displaying a variety of antibody molecules. These modified antibodies can be produced with known methods. Examples of the chimeric antibody include an antibody having variable and constant regions of different species. Specific examples thereof include an antibody including the heavy and light chain variable regions of a mouse antibody introduced in the heavy and light chain constant regions of a human antibody. To obtain such an antibody, DNA encoding the variable region of a mouse antibody is ligated to DNA encoding the constant region of a human antibody. This ligation product is then incorporated into an expression vector. This vector can be introduced into a host so as to produce the antibody.

The humanized antibody is, for example, an antibody including complementarity-determining regions (CDRs) in a human antibody substituted for CDRs in the heavy or light chain of a non-human antibody such as a mouse antibody. A general gene recombination approach thereof has also been known (e.g., Jones et al., Nature 321: 522-525 (1986)). Specifically, a DNA sequence is designed to ligate CDRs in a mouse antibody to framework regions (FRs) in a human antibody. This DNA sequence is synthesized by PCR from several oligonucleotides produced to have terminal overlap portions. The obtained DNA is ligated to DNA encoding the constant region of a human antibody. This ligation product is subsequently incorporated into an expression vector. This vector is introduced into a host so as to produce the antibody. The FRs of a human antibody ligated via CDRs are selected in such a way that the complementarity-determining regions form favorable antigen-binding sites. The humanized antibody may contain an amino acid residue contained in neither of the CDR nor framework sequences introduced in the recipient antibody. Such an amino acid residue is usually introduced for more accurately optimizing the ability of the antibody to recognize/bind to an antigen. For example, amino acids in the framework regions in the variable region of the reconstituted human antibody may be substituted, if necessary, in such a way that the complementarity-determining regions of the antibody form appropriate antigen-binding sites (Sato, K. et al., Cancer Res. (1993) 53, 851-856).

Alternatively, the antibody of the present invention may be an antibody fragment having the antigen-binding site of the antibody or a modified fragment thereof. The "antibody fragment" refers to a portion of the full-length antibody and is generally a fragment including the antigen-binding region or variable region of the antibody. The antibody fragment described in the present invention means a partial region of a monoclonal antibody. Specific examples thereof include F(ab')2, Fab', Fab, Fd, Fv (variable fragment of antibody), scFv (single chain Fv), dsFv (disulfide stabilized Fv) and a single domain antibody (dAb) including a heavy chain variable region (VH) or light chain variable region (VL).

Acquisition of Anti-Photocrosslinking Group Antibody

The antibody having the ability to recognize a photocrosslinking group (anti-photocrosslinking group antibody) according to the present invention can be acquired by methods appropriately selected from conventional antiserum preparation techniques and monoclonal antibody preparation techniques using cell fusion. For example, a hapten having a photocrosslinking group to be bound is prepared, because the photocrosslinking group is a low-molecular-weight compound. The hapten is bound with a carrier protein KLH (Keyhole Limpet Haemocyanin) to prepare an immunogen. An appropriate immune animal is immunized with this immunogen. At the point in time when an increase in antibody titer is confirmed, the antibody can be collected from the serum. The immunization can be performed by diluting the photocrosslinking group-carrier protein conjugate as an immunogen to an appropriate concentration in an appropriate solvent (e.g., a saline) and intravenously or intraperitoneally administering this solution to an immune animal. Furthermore, a Freund's complete adjuvant may also be used and administered thereto, if necessary. In a general method, the administration to the animal is performed approximately 3 to 4 times at 1- to 2-week intervals. The animal thus immunized is dissected on the third day after the final immunization. Spleen cells are obtained from the excised spleen and used as immunocytes. The photocrosslinking group of the present invention is inactivated by a UV light (350 nm). Therefore, it is desired that procedures should be conducted in a dark room until immunization.

The obtained antibody may be a polyclonal antibody. However, when the antibody is obtained as a monoclonal antibody, a clone more excellent in specificity to a photocrosslinking group can be selected. The monoclonal antibody can be obtained by cloning monoclonal antibody-producing cells. In general, immunoglobulin-producing cells such as the spleen cells collected from the immune animal can be fused with cancer cells to form hybridomas (Gulfre G., Nature 266. 550-552, 1977). Examples of the cancer cells include: mouse-derived myeloma cells P3/X63-AG8.653 (ATCC No. CRL-1580), P3/NSI/1-Ag-4-1 (NS-1), P3/X63-Ag8.U1 (P3U1), SP2/0-Ag14 (Sp2/O, Sp2), NS0, PAI, F0 and BW5147; rat-derived myeloma cells 210RCY3-Ag.2.3.; and human-derived myeloma cells U-266AR1, GM1500-6TG-A1-2, UC729-6, CEM-AGR, D1R11 and CEM-T15.

The monoclonal antibody-producing cells can be screened by culturing the cells in a titer plate and measuring the reactivity of the culture supernatant with observable growth in the well to the photocrosslinking group. In this measurement, for example, enzyme immunoassay (e.g., RIA (radio immunoassay) or ELISA (enzyme-linked immunosorbent assay)) and immunoprecipitation can be utilized. The binding properties to the photocrosslinking group can also be measured quantitatively by use of a surface plasmon resonance (SPR) apparatus. In evaluation using the SPR apparatus, measurement can be achieved by directly immobilizing an adjuvant protein onto the gold surface of a sensor through physical adsorption or chemical crosslinking.

Antibody Fragment

The antibody fragment described in the present invention means a partial region of a monoclonal antibody. Specific examples thereof include F(ab')2, Fab', Fab, Fd, Fv (variable fragment of antibody), scFv (single chain Fv), dsFv (disulfide stabilized Fv) and a single domain antibody (dAb) including a heavy chain variable region (VH) or light chain variable region (VL).

In this context, the "F(ab')2" and "Fab'" fragments mean antibody fragments generated by digesting the antibody at a position upstream or downstream of the inter-heavy (H) chain disulfide bond in the hinge region. This antibody fragment can be obtained by treating the antibody with protease such as pepsin or papain. For example, treatment with papain cleaves IgG at a position upstream of the inter-H chain disulfide bond in the hinge region. As a result, two homologous fragments are obtained in which a light chain (L chain) fragment comprising a light chain variable region (VL) and a light chain constant region (CL) and a heavy chain (H chain) fragment comprising a heavy chain variable region (VH) and a heavy chain constant region 1 (CH1) are linked together via a disulfide bond at the C-terminal region. These two homologous fragments are respectively referred to as Fab'. Alternatively, treatment with pepsin cleaves IgG at a position downstream of the inter-H chain disulfide bond in the hinge region. As a result, an antibody fragment slightly larger than those two Fab' fragments connected by the hinge region can be produced. This antibody fragment is referred to as F(ab')2.

Thus, the photocrosslinking group-recognizing antibody of the present invention may be the Fab' or F(ab')2 fragment. Alternatively, the antibody of the present invention may be an Fd fragment comprising VH and the CH1 domain linked together.

Furthermore, the antibody of the present invention may be Fv (variable fragment of antibody) or a portion thereof. For example, the antibody of the present invention may be a heavy chain variable region (VH) or light chain variable region (VL) constituting Fv or a portion thereof. On the other hand, a single chain Fv (scFv) can also be utilized which is a complex of VH and VL linked via a peptide including several amino acids derived from the carboxy terminus of one of these regions and from the amino terminus of the other. It is desired that a linker including one or more amino acid(s) should be provided between VH and VL (not in particular order) forming the scFv fragment. Furthermore, it is important to design the residue length of the amino acid linker to be free from binding force that prevents structure formation required for the binding of VH or VL to an antigen. As a specific example, the amino acid linker is generally 5 to 18 residues in length. An amino acid linker of 15 residues has been used and studied most frequently. These fragments can be obtained by a genetic engineering approach.

Furthermore, the antibody of the present invention may be a VH or VL single domain antibody (dAb). In general, the single domain structure is often unstable. Thus, this antibody fragment may be stabilized by chemical modification such as PEG modification. Alternatively, the antibody of the present invention may be a llama heavy chain antibody variable region VHH (J. Mol. Biol, 311: p 123, 2001) or a Nurse shark immunoglobulin-like molecule variable region IgNAR. These heavy chain antibodies have been known to exist and function in vivo. Furthermore, the VH or VL region of an antibody molecule (typically, derived from a human or mouse) including heavy and light chains is used as each single domain, as illustrated in FIGS. 1 to 4. In this case, a variation may be introduced, for example, into the VH-VL interface with reference to the corresponding portion of the heavy chain antibody so as to improve stability.

The photocrosslinking group-recognizing site can include at least one selected from (1) an antibody heavy chain variable region (VH), a variant thereof and a portion thereof and (2) an antibody light chain variable region (VL), a variant thereof and a portion thereof. Examples of a set of complementarity-determining regions in the antibody heavy chain variable region (VH) that can be used can include proteins selected from an amino acid set of SEQ ID NOs: 1 to 3 and an amino acid set of SEQ ID NOs: 4 to 6. Examples of a set of complementarity-determining regions in the antibody light chain variable region (VL) that can be used can include proteins selected from an amino acid set of SEQ ID NOs: 7 to 9 and an amino acid set of SEQ ID NOs: 10 to 12. These sequences are shown below.

```
PM1-VH CDR
SEQ ID NO: 1 (H chain CDR1)
S H N M L

SEQ ID NO: 2 (H chain CDR2)
G I Y P G D G D T S Y N Q N F K G

SEQ ID NO: 3 (H chain CDR3)
W D L L C F D Y

PM2-VH CDR
SEQ ID NO: 4 (H chain CDR1)
S Y W M H

SEQ ID NO: 5 (H chain CDR2)
Y I N P S T G Y T E Y N Q K F

SEQ ID NO: 6 (H chain CDR3)
N G N G Y

PM1-VL CDR
SEQ ID NO: 7 (L chain CDR1)
R A S S S I S Y M H

SEQ ID NO: 8 (L chain CDR2)
A S Q S I S
```

-continued

SEQ ID NO: 9 (L chain CDR3)
Q Q W S N S P P Y T

PM2-VL CDR
SEQ ID NO: 10 (L chain CDR1)
T A S Q S I S Y V V

SEQ ID NO: 11 (L chain CDR2)
S A S N L A S

SEQ ID NO: 12 (L chain CDR3)
G Q G Y S P L T

An antibody fragment including one or more amino acid sequence(s) derived from these amino acid sequences of SEQ ID NOs: 1 to 12 with the deletion, substitution or addition of their respective one or several amino acids and having binding properties to a photocrosslinking group can be utilized in the same way as long as the antibody fragment is functionally equivalent thereto.

The CDR regions including the amino acid sequences can be inserted in between framework regions (FRs) to obtain a V or L chain of interest. SEQ ID NOs: 13 to 16 (amino acid sequence) and SEQ ID NOs: 21 to 24 (DNA sequence) respectively represent one example of a sequence including CDR regions arranged between FRs. The 31st to 35th positions of the amino acid sequence of SEQ ID NO: 13 represent the H chain CDR1 including the amino acid sequence of SEQ ID NO: 1. Hereinafter, the amino acid sequence of SEQ ID NO: 13 also includes the H chain CDR2 including the amino acid sequence of SEQ ID NO: 2 and the H chain CDR3 including the amino acid sequence of SEQ ID NO: 3. Furthermore, the amino acid sequences of SEQ ID NOs: 14 to 16 include the CDR region including each of the amino acid sequences of SEQ ID NOs: 4 to 12. The framework regions are not particularly limited as long as antibody functions of interest are obtained. The framework regions can be selected according to purposes from a variety of frameworks known in the art and combined with CDR regions.

Acquisition of Photocrosslinking Group-Recognizing Antibody Fragment

Acquisition using enzyme treatment The antibody can also be treated with a certain enzyme to obtain an antibody fragment having the antigen-binding site of the antibody and the ability of the antibody to bind to an antigen to some extent. For example, the obtained antibody can be treated with papain to obtain an Fab fragment or an analog thereof. Alternatively, the antibody is treated with pepsin to obtain an F(ab')2 fragment or an analog thereof. The antibody fragment is also prepared by a chemical decomposition method, in addition to this enzymatic approach. Any of these antibody fragments having the ability to bind to a photocrosslinking group can also be used without any problem.

The Fab', Fv and VH or VL dAb fragments of the present invention may be obtained by a method using a genetic engineering approach. For example, a gene library of the VH or VL region is prepared. These genes are comprehensively expressed as proteins. In this method, proteins having binding properties to a photocrosslinking group or to a target substance are selected according to their genes. The gene library can be obtained from, for example, cord blood, tonsils, bone marrow, peripheral blood cells or spleen cells. For example, mRNA is extracted from human peripheral blood cells, and cDNA is synthesized from this mRNA. Next, a cDNA library of human VH or VL is prepared with a human VH- or VL-encoding sequence as a probe. For example, primers capable of extensively amplifying each of human VH families (VH1 to VH7) or primers capable of amplifying human VL are known in the art. RT-PCR using these primers appropriately combined for each of VH and VL is performed to obtain genes encoding VH and VL. Alternatively, a phage display method may be used. In the phage display method, a gene library encoding VH, VL or a complex including these regions (e.g., Fab or scFv) is bound with a gene encoding a phage coat protein to prepare a phagemid library. E. coli is transformed with the phagemid library. These genes are expressed as phages having a variety of VH or VL regions as a portion of the coat proteins. The phages can be used to select, in the same way as above, those having binding properties to a photocrosslinking group or to a target substance. The gene encoding VH or VL displayed as a fusion protein on the phage is encoded by the phagemid in the phage and can therefore be identified by DNA sequencing.

Object to be Bound Having Photocrosslinking Group Used in Selection of Library

An object to be bound used for selecting an anti-photocrosslinking group antibody fragment by panning can be selected variously for use from substances having a photocrosslinking group at least a portion of their surfaces. For selecting an anti-photocrosslinking group antibody fragment by panning, it is more desired that only the photocrosslinking group should be present on the surface of the object to be bound. This is because proteins adsorbed onto substances other than the photocrosslinking group are prevented from contaminating. A material for an internal core base other than the surface can be selected for use from a variety of known materials. The object to be bound may have any surface as long as a molecule including a photocrosslinking group can be immobilized directly or indirectly on the surface. The object to be bound can be subjected to a treatment for suppressing non-specific adsorption. Moreover, it is desired that panning selection should be performed, as much as possible, in a dark room or within the place surrounded by yellow curtains that filter out a UV light. This is because the photocrosslinking group of the present invention is prevented from being inactivated.

The present invention also encompasses a nucleic acid encoding the photocrosslinking group-recognizing antibody. The present invention further encompasses a construct including a nucleic acid serving as a gene vector. This construct for expressing the photocrosslinking group-recognizing antibody is used to transform a host cell (e.g., conventionally known E. coli-, yeast-, mouse- or human-derived cells for protein expression). As a result, the photocrosslinking group-recognizing antibody can be expressed from the host cell. The photocrosslinking group-recognizing antibody of the present invention, which can be expressed by the single expression vector, may be selected for design from the whole antibody molecule, antibody fragments thereof (F(ab')$_2$, Fab, Fv (scFv), VH and VL) and complexes thereof. When plural antibody fragments are encoded by one expression vector, the antibody fragments can be expressed each individually as independent polypeptide chains. Alternatively, a vector may be constituted to express the antibody fragments as one polypeptide chain including the domains bound consecutively or via amino acids.

To constitute the vector for expression of the photocrosslinking group-recognizing antibody of the present invention, the vector can be designed and constructed by integrating constitutions necessary for transgene expression, such as known promoters, according to a host cell selected. The vector constitution can be constructed with reference to the constitutions such as known promoters according to a host cell selected. Alternatively, when *E. coli* is used as a host cell, the photocrosslinking group-recognizing antibody of the present invention or a construct thereof, which is obtained as a foreign gene product, is immediately removed to the outside of the cytoplasm. This can reduce decomposition by protease. It is also known that even if this foreign gene product is toxic to the bacterial cell, its influence can be reduced by secreting the foreign gene product to the outside of the cell. Most known proteins secreted through a cytoplasmic membrane or inner membrane usually have a signal peptide at the N-terminus of their precursors. The precursors undergo the cleavage of the signal peptide by signal peptidase in the secretion process and become mature proteins. Most signal peptides have basic amino acids, hydrophobic amino acids and cleavage sites by signal peptidase located at the N-terminus thereof.

A nucleic acid encoding a conventionally known signal peptide (typically, pelB) can be arranged at the 5' end of the nucleic acid encoding the photocrosslinking group-recognizing antibody of the present invention so as to secrete and express the photocrosslinking group-recognizing antibody.

Alternatively, plural polypeptide chains including the photocrosslinking group-recognizing antibody (including plural antibody fragments) of the present invention may be inserted each independently into one vector. In this case, a nucleic acid encoding pelB can be arranged at the 5' end of a nucleic acid encoding each domain or polypeptide chain so as to promote secretion. To express a polypeptide chain including one or more domain(s), a nucleic acid encoding pelB can be arranged in the same way at the 5' end of the polypeptide chain so as to promote secretion. The photocrosslinking group-recognizing antibody of the present invention thus fused at the N-terminus with the signal peptide can be purified from the periplasmic fraction or medium supernatant.

The obtained antibody can be purified evenly. Separation and purification methods usually used for proteins may be used in antibody separation and purification. For example, chromatography columns, filters, ultrafiltration, salting-out, dialysis, polyacrylamide gel electrophoresis for preparation and isoelectric focusing can be selected and combined appropriately to separate and purify the antibody. Examples of chromatography include affinity chromatography, ion-exchange chromatography, hydrophobic chromatography, gel filtration, reverse phase chromatography and adsorption chromatography. These chromatography techniques can be used with liquid phase chromatography such as HPLC or FPLC.

When the photocrosslinking group-recognizing antibody is obtained and purified as a complete antibody, examples of an affinity purification column include protein A and protein G columns.

Considering convenient antibody fragment expression and purification procedures, a tag for affinity purification may be arranged in a genetic engineering manner at the N- or C-termini of polypeptide chains forming a variety of antibody fragments. Examples of the tag for purification include a histidine tag comprising six consecutive histidine residues (hereinafter, referred to as His×6) and the glutathione-binding site of glutathione-S-transferase. Examples of a tag introduction method include: a method including introducing a nucleic acid encoding the purification tag into the 5' or 3' end of the nucleic acid encoding the photocrosslinking group-recognizing antibody in the expression vector; and a method using a commercially available vector for purification tag introduction.

Alternatively, the antibody may be purified with an antigen-immobilized carrier by use of binding properties to an antigen.

Hereinafter, a method for producing the photocrosslinking group-recognizing antibody of the present invention by use of the expression vector will be described. The photocrosslinking group-recognizing antibody of the present invention or a polypeptide chain serving as a component thereof can be produced by transforming a conventionally known host cell for protein expression with the vector for expression of the photocrosslinking group-recognizing antibody designed according to the host cell. Specifically, the photocrosslinking group-recognizing antibody or the polypeptide chain serving as a component thereof is synthesized within the host cell by use of the protein synthesis system within the host cell. Then, the protein of interest accumulated or secreted to the inside or outside of the host cell is purified from the inside of the cell or cell culture supernatant. The purified protein is available in application of interest. For example, when *E. coli* is used as a host cell, a nucleic acid encoding a conventionally known signal peptide (typically, pelB) is located at the 5' end of a nucleic acid encoding the photocrosslinking group-recognizing antibody of the present invention. The protein expressed therefrom can have a form easily secreted and expressed to the outside of the cytoplasm.

When plural polypeptide chains constituting the photocrosslinking group-recognizing antibody of the present invention are expressed by one expression vector, a nucleic acid encoding pelB is arranged at the 5' end of a nucleic acid encoding each polypeptide chain. The secretion of the proteins to the outside of the cytoplasm can be promoted during their expression. The photocrosslinking group-recognizing antibody thus fused at the N-terminus with the signal peptide can be purified from the periplasmic fraction or medium supernatant. The antibody fused with the His tag and GST as a purification tag can be purified by a purification method using a nickel chelate column and a glutathione-immobilized column, respectively.

The photocrosslinking group-recognizing antibody expressed within the bacterial cell may be obtained as insoluble granules. In this case, the bacterial cell obtained from the culture solution is disrupted by French press or ultrasonication. The insoluble granules can be obtained by centrifugation from the cell homogenate. The obtained insoluble granular fraction is solubilized with a buffer solution including a conventionally known denaturant containing urea and guanidine hydrochloride. Then, the solubilized fraction can be column-purified under denaturation conditions in the same way as above. The obtained column elution fraction can be subjected to refolding procedures for removing the denaturant and reconstructing active structure. The refolding method can be selected appropriately for use from conventionally known methods. Specifically, for example, a stepwise dialysis or dilution method may be used according to the protein of interest.

Plural domains or polypeptide chains of the photocrosslinking group-recognizing antibody of the present invention may be expressed within the same host cell or separately in different host cells, combined and then converted into a complex formed thereby.

Furthermore, the protein may be expressed in vitro by the vector encoding the photocrosslinking group-recognizing antibody of the present invention by use of a cell extract. Examples of the cell extract that can be used include *E. coli*, wheat germ and rabbit reticulocytes. However, the protein synthesis using a cell-free extract is generally performed under reduction conditions. Therefore, some treatment for forming a disulfide bond in the antibody can be performed.

Antibody Fragment Protein Expression

DNA encoding the photocrosslinking group-recognizing antibody is cleaved with desired restriction enzymes, for example, NcoI/NheI for the case described above, to obtain DNA encoding a photocrosslinking group-recognizing antibody fragment. This DNA can be introduced into a plasmid for protein expression conventionally known in the art according to a host cell to obtain an antibody fragment. For example, the antibody fragment of interest may be collected from the extracellularly expressed or periplasmic fraction of E. coli. In this case, a conventionally known signal peptide can be introduced upstream of the antibody fragment-encoding gene. Examples of the signal peptide include pelB. Alternatively, a conventionally known tag for purification may be fused with the gene for easily purifying the protein of interest from the culture supernatant or bacterial cell fraction after expression. Specifically, six histidine residues (His×6) or the glutathione-binding site of glutathione-S-transferase can be introduced into the gene to form a fusion protein. This fusion protein with the His tag can be purified easily with a metal (e.g., nickel) chelate column. The fusion protein with the GST tag can be purified with a column including a glutathione-immobilized carrier (e.g., Sepharose).

Alternatively, when the protein of interest expressed within the bacterial cell cannot be obtained as insoluble granules, the protein can be solubilized with a conventionally known buffer solution containing urea and guanidine hydrochloride and then subjected to refolding. The refolding method can be selected appropriately for use from conventionally known methods. Specifically, for example, a stepwise dialysis or dilution method may be used according to the protein of interest.

Even an amino acid sequence derived from the amino acid sequence of the thus-obtained antibody, fragments thereof (e.g., Fab, (Fab')$_2$, Fd, VH or VL) or complexes thereof with the deletion, substitution or addition of one or several amino acids is encompassed within the scope of the present invention as long as the amino acid sequence exhibits binding properties to a photocrosslinking group.

Substrate and Structure

A structure can be obtained from the anti-photocrosslinking group antibody and a substrate having a photocrosslinking group forming at least a portion of the surface. This structure is available in a variety of applications. This substrate, which has a photocrosslinking group arranged on at least a portion of its surface, may be made of any material and have any form as long as the substrate can form the structure of the present invention. The photocrosslinking group can be formed on the substrate by use of reaction known in the art. Examples of the reaction include the reaction of a glass surface with a silane coupling agent, the reaction of a functional group on a plastic surface with an active halide, the reaction of a cellulose resin with isocyanates, and physical adsorption. For example, the reaction of the group introduced in advance on the substrate surface can be selected according to the type of the substrate from combinations of nucleophilic groups (e.g., amino and hydroxyl groups) with electron-withdrawing groups (e.g., carboxyl, ester, isocyanate and isothiocyanate groups, conjugate ketone, acrylic ester, vinylsulfone, acid anhydrides, acyl halide and sulfonyl halide), combinations using vital reaction (biotin-avidin and substrate-enzyme) and combinations of gold with thiol. Alternatively, materials for performing the reactions can be arranged in a portion of the substrate. This arrangement can be achieved, for example, by use of a stamper or by patterning. The substrate may be made of any material as long as the substrate can form the structure of the present invention. The material includes any one or more member(s) selected from metals, metal oxides, inorganic semiconductors, organic semiconductors, glasses, ceramics, natural polymers, synthetic polymers and plastics or includes a complex thereof. The substrate used in the present invention may have any form as long as the substrate can form the structure of the present invention. The form includes any one or more form(s) selected from plate-like, particle-like, porous, protruding, fibrous, cylindrical and mesh-like forms.

The substrate material and the substrate made thereof that can be used in the present invention are exemplified by those disclosed in Japanese Patent Application Laid-Open No. 2005-312446. Specifically, the substrate material that can be used is any one or more member(s) selected from metals, metal oxides, inorganic semiconductors, organic semiconductors, glasses, ceramics, natural polymers, synthetic polymers and plastics, or is a complex thereof. Examples of the substrate form can include any one or more form(s) selected from plate-like, particle-like, porous, protruding, fibrous, cylindrical and mesh-like forms. Of course, the substrate material and form are not limited to these materials and forms. The substrate of the present invention may have a size variously selected according to its use.

Kit for Detecting Target Substance

The constitution of the anti-photocrosslinking group antibody of the present invention to which binding properties to a target substance are imparted can be used to obtain a kit for detecting a target substance. For example, the kit for detecting a target substance can include: the substrate and the anti-photocrosslinking group antibody for forming the structure; and a detection unit for detecting the binding of a target substance to the structure. A method for immobilizing the anti-photocrosslinking group antibody onto the substrate by crosslinking through light irradiation will be described later. The anti-photocrosslinking group antibody in the present kit can be used as, for example, a form displaying a sugar chain that binds to a variety of antibodies. Specifically, a target substance can serve as a sugar chain-binding substance for the antibody. The target substance can be detected by detecting the binding formation between the target substance and the antibody by a physical or chemical approach. The binding between the target substance and the anti-photocrosslinking group antibody can be detected by measuring a change in physical quantity such as an optical, electrical or thermal change.

Examples of the constitution that can be used to which binding properties to a target substance (particularly, an antigen) are imparted can include constitution used as a photocrosslinking group-recognizing complex protein described later.

Surface Plasmon Resonance Apparatus and Quartz Crystal Oscillator Microbalance Apparatus The binding of a target substance to the protein having the ability to recognize a photocrosslinking group can be measured quantitatively with, for example, a conventionally known surface plasmon resonance (SPR) measurement apparatus or quartz crystal oscillator microbalance (QCM). In general, surface plasmon resonance is a method by which a change in refractive index on a thin gold film provided on a glass base is measured based on a change in resonance angle generated by the resonance (surface plasmon resonance) between free electrons on the gold thin film and an evanescent wave generated on the glass-gold interface by incident light from a glass side at an incident angle of not more than the total reflection angle. The measured change in refractive index can be converted into the amount of a target substance bound, and then evaluated. The evaluation can be conducted by preparing a chip having a photocrosslinking group formed chemically or physically on a thin gold film. In general, QCM can quantify and evaluate biomolecular interaction occurring on a gold electrode surface on a crystal oscillator, with a change in crystal frequency as an index. As a result, the change in frequency can be evaluated as the amount of the target protein bound to gold. The evaluation can be conducted by preparing a chip having a photocrosslinking group formed chemically or physically on a thin gold film, as in SPR.

Dissociation Constant ($K_D$)

A "dissociation constant ($K_D$)" refers to a value determined by dividing a "dissociation rate (kd)" value by a "binding rate (ka)" value. This constant can be used as an index for representing the affinity of a monoclonal antibody or fragments thereof for a photocrosslinking group. This constant can be analyzed according to a variety of methods. In the present invention, the dissociation constant was obtained by analysis from a binding curve obtained with a measurement apparatus Biacore 2000 (manufactured by Biacore) according to the analysis software included in the apparatus.

Photocrosslinking Group-Recognizing Complex Protein

The photocrosslinking group-recognizing complex protein of the present invention can be provided to include two or more domains. One or more of the domains have the anti-photocrosslinking group antibody thus constituted. However, not all the domains have the anti-photocrosslinking group antibody. At least one domain is provided to form a target substance-biding domain having the ability to recognize a target substance. In the present complex protein, the domain forming a target substance-binding domain may be a molecule having any structure as long as the molecule can specifically recognize and bind to a target substance. This domain can include a protein, sugar chain, nucleic acid or lipid. Examples of the protein include an ankyrin-structure molecule (Andreas Pluckthun et al., Nature Biotechnology Vol 22, No. 5, 575-582 (2004)), an Affilin molecule (Scil Proteins), an Affibody molecule (Per-Ake Nygren et al., Proteins: Structure, Function, and Genetics 48, 454-462 (2002)), fibronectin Type III 10th, lipocalin, GFP, lectin, thioredoxin and Omp (outer membrane protein) molecules, fragments thereof or derivatives thereof. These molecules have non-antibody structure expected to have affinity that exceeds that of antibodies and molecular recognition that cannot be recognized by antibodies and can specifically bind to a target substance by genetic engineering modification. The domain can have at least a portion of an antibody. This complex protein can be exemplified by those having the following constitutions: (a) a complex protein having a first domain including the anti-photocrosslinking group antibody thus constituted, and a second domain including a protein having a target substance-binding site; and (b) a complex protein further having, in addition to the first and second domains, at least one of a third domain forming a complex with the first domain and a fourth domain forming a complex with the second domain.

The binding properties of the first to fourth domains to a substance to be bound can be set each independently. Among these domains, two or more of the domains may have the same binding properties. Alternatively, these domains may include domains having different binding properties. Furthermore, at least two members selected from the first to fourth domains may be included in the same polypeptide chain. Examples of such constitution can include the following constitutions: (1) constitution in which the first and second domains form one polypeptide chain; (2) constitution in which the first and second domains are bound via one or more amino acid(s); (3) constitution in which the third and fourth domains form one polypeptide chain; (4) constitution in which the third and fourth domains are bound via one or more amino acid(s); (5) constitution comprising a first polypeptide chain including the first and second domains and a second polypeptide chain including the third and fourth domains; (6) constitution comprising the first polypeptide chain including the first and second domains and a third polypeptide chain including the third and second domains; (7) constitution comprising the first polypeptide chain including the first and second domains and a fourth polypeptide chain comprising the first and fourth domains; (8) constitution comprising one polypeptide chain including at least the first, second and third domains; (9) constitution comprising one polypeptide chain including at least the first, second and fourth domains; and (10) constitution comprising one polypeptide chain including the first to fourth domains.

The protein as a component of the photocrosslinking group-recognizing complex protein refers to a molecule including at least one or more polypeptide chain(s) formed by at least two or more amino acids bound together and having structure in which the polypeptide chain(s) is refolded so as to form particular three-dimensional structure. This protein can exert its unique functions (e.g., conversion and molecular recognition) by virtue of this structure. The photocrosslinking group-recognizing complex protein of the present invention has at least one or more photocrosslinking group-binding site(s) and further has at least one or more target substance-binding site(s), as described above. Thus, this complex protein exhibits multivalent or multiple binding specificity. In the constitution that can be used, the first domain having a photocrosslinking group-binding site includes at least a portion of an antibody light chain variable region (VL) or heavy chain variable region (VH), while the second domain having a target substance-binding site includes at least a portion of VH or VL (hereinafter, photocrosslinking group-binding VH and VL are referred to as VH(P) and VL(P), respectively, and target substance-binding VH and VL are referred to as VH(T) and VL(T)).

The antibody heavy chain variable region (VH) and light chain variable region (VL) are variable regions in the antibody heavy and light chains, respectively, as described above. The antibody heavy chain variable region (VH) or light chain variable region (VL) generally comprises approximately 110 amino acids. These regions assume cylindrical structure in which layer structure including antiparallel β sheets is formed. This layer structure is bound with one S—S bond to form a very stable structure. The variable region (VH or VL) has been known to have portions called complementarity-determining regions (CDRs) that determine the diversity of antigen binding of the antibody. Three CDRs are present in each of VH and VL chains and interposed between framework regions including relatively less diverse amino acid sequences. The CDRs can recognize the spatial position of a functional group in a target recognition site so as to achieve higher specific molecular recognition.

Hereinafter, one example of the photocrosslinking group-recognizing complex protein of the present invention will be described. The minimal unit of the photocrosslinking group-recognizing complex protein of the present invention includes the first and second domains. FIGS. 1A to 1D illustrate schematic diagrams thereof. Examples of combinations of the first and second domains include VH(P)-VH(T), VH(P)-VL(T), VL(P)-VH(T) and VL(P)-VL(T) combinations. The protein represented by (P) is the anti-photo-crosslinking group antibody protein. In the photocrosslinking group-recognizing complex protein according to this example, the first and second domains do not form complementary binding sites and independently bind to a photocrosslinking group and a target substance, respectively. The first and second domains may be independent polypeptide chains or may be a polypeptide chain including the domains bound consecutively. However, in the exemplary embodiment, a polypeptide chain including the polypeptide chains bound consecutively can be formed for simplifying production steps and exhibiting the functions. In a polypeptide chain including the first and second domains bound consecutively, the first and second domains may be linked directly or via a linker including one or more amino acid(s). The amino acid linker can include 1 to 10 amino acids. Particularly, a linker including 1 to 5 amino acids can be used. When the linker is 11 to 15 amino acids in length, the first and second domains sometimes form complementary binding (converted into scFv) between these domains due to few limitations by arrangement. It has been known that the addition of structural constraints attributed to a shorter linker between the domains is effective for suppressing this complementary complex formation between VH and VL. On the other hand, an intentionally longer linker of 11 residues or more may be provided for preventing steric hindrance to the binding properties to a target substance. In this case, it is desired that VH or VL including, for example, a heavy chain antibody antigen-recognizing site VHH or VH-VL interface modified in a genetic engineering manner should be used. It is desired that each of the first and second domains should not undergo the influence of a structural change brought about by its binding to a photocrosslinking group or to a target substance on the desired ability to bind to a photocrosslinking group or to a target substance. Therefore, secondary structure such as α-helix may be imparted to the linker, or a polypeptide domain irrelevant to the original desired binding properties may be inserted into the protein, without making significant influences on desired properties or productivity.

Furthermore, the photocrosslinking group-recognizing complex protein of the present invention may also include the third domain forming a complex with the first domain or/and the fourth domain forming a complex with the second domain, as described above. Each of these third and fourth domains can include at least a portion of VH or VL. It is more desired that the third domain should form a complex with the first domain so as to form complementary photocrosslinking group-binding sites with the first domain. For example, when the first domain is VH(P) as illustrated in the schematic diagram of FIG. 2A, the third domain can be VL capable of forming Fv with the first domain. Particularly, the first and third domains can form photocrosslinking group-binding sites in alliance with each other. Such Fv formation of the first and third domains structurally stabilizes the protein and can be expected to suppress reduction in functions attributed to a structural change. The formation of photocrosslinking group-binding sites by the third and first domains in alliance with each other can be expected to further improve the ability to bind to a photocrosslinking group (e.g., improvement in binding rate and reduction in dissociation rate).

The first and third domains may be provided as each independent polypeptide chain as illustrated in FIG. 2B or as polypeptide chains linked together (e.g., the third domain, the first domain and the second domain linked in this order as illustrated in the schematic diagram of FIG. 2B; the constitution can be determined appropriately so as to exert the abilities to bind to a photocrosslinking group and to a target substance). In another example, the domains may be constituted as illustrated in the schematic diagram of FIG. 3. Specifically, this complex protein includes a polypeptide chain including the first and second domains and a polypeptide chain including the third and second domains. In this case, the Fv or Fv-like complex formed by the first and third domains binds to a photocrosslinking group, while the first domain functions with the second domain as a target substance-binding anchor.

Figure 4B:
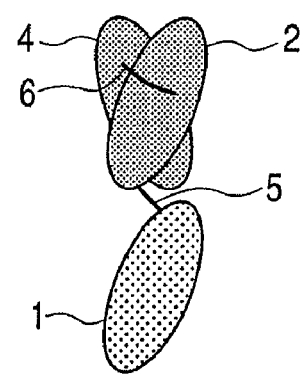

Alternatively, the photocrosslinking group-recognizing complex protein of the present invention may also include the fourth domain forming a complex with the second domain. This fourth domain includes at least a portion of VH or VL. It is desired that the fourth domain should complementarily form target substance-binding sites together with the second domain. For example, when the second domain is VL as illustrated in the schematic diagram of FIG. 4A, the fourth domain can be VH capable of forming Fv with the second domain. Particularly, the second and fourth domains can form target substance-binding sites in alliance with each other. Alternatively, a polypeptide chain including the first, second and fourth domains linked together may be formed as illustrated in the schematic diagram of FIG. 4B. In the constitution of FIG. 4B, each domain can be selected in such a way that the first domain binds to a substrate having a photocrosslinking group on at least a portion of the surface, and the second and fourth domains bind to a target substance. In this constitution, particularly, the influence of an irreversible structural change attributed to the binding of the first domain with the substrate on the abilities of the second and fourth domains to a target substance can be minimized by appropriately designing the linker.

Figure 5:
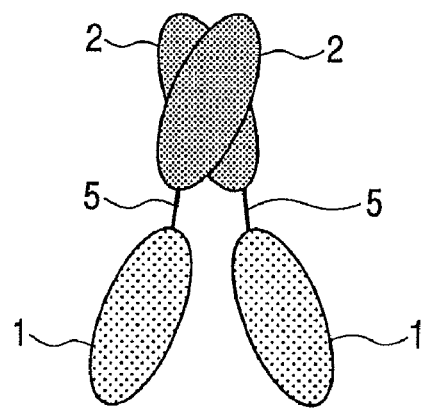
FIG. 5 is a diagram schematically illustrating the constitution of a structure according to one example of a complex protein of the present invention.

Furthermore, the domains may be constituted as illustrated in the schematic diagram of FIG. 5. Specifically, this complex protein includes a polypeptide chain including the first and second domains and a polypeptide chain including the first and fourth domains. In this case, the Fv or Fv-like complex formed by the second and fourth domains binds to a target substance, while the first domain functions with both the polypeptide chains as photocrosslinking group-binding anchors.

Figure 6:
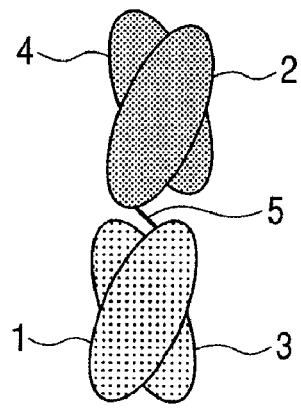
FIG. 6 is a diagram schematically illustrating the constitution of a structure according to one example of a complex protein of the present invention.
Figure 7:
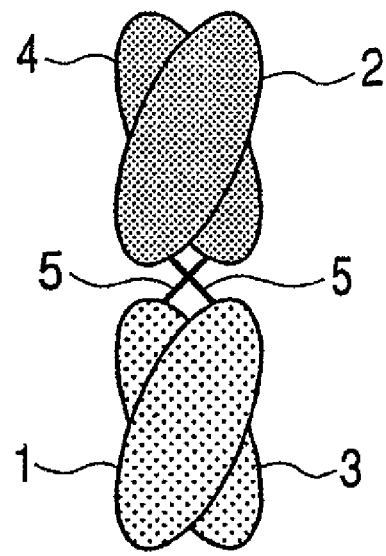
FIG. 7 is a diagram schematically illustrating the constitution of a structure according to one example of a complex protein of the present invention.
Figure 8:
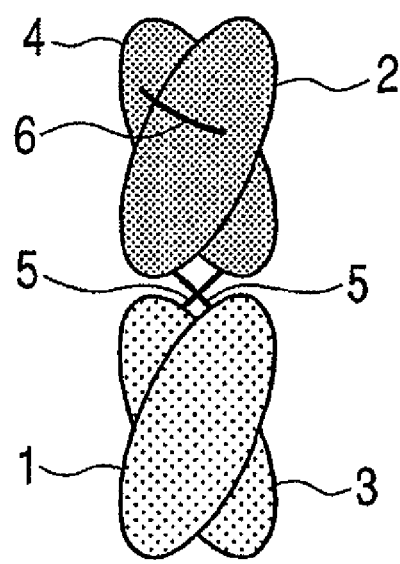
FIG. 8 is a diagram schematically illustrating the constitution of a structure according to one example of a complex protein of the present invention.

Alternatively, the present photocrosslinking group-recognizing complex protein may include both the third and fourth domains as components. The third and fourth domains may be each independent polypeptide chain as illustrated in the schematic diagram of FIG. 6 or may be polypeptide chains linked together as illustrated in the schematic diagram of FIG. 7. For the polypeptide chains linked together, the third and fourth domains may be linked directly or via a linker including one or more amino acid(s) as illustrated in FIG. 7. Alternatively, the first to fourth domains may be linked within one polypeptide chain as illustrated in the schematic diagram of FIG. 8. In this case, the domains can be arranged in such a way that the first and third domains can form a complex and bind to a photocrosslinking group, and the second and fourth domains can form a complex and bind to a target substance. Therefore, linkers can be provided between the domains. For example, 1 to 5 amino acids are provided between the first and second domains and between the third and fourth domains. Fifteen to 25 amino acids are provided between the second and third amino acid domains. In similar constitution, the interchange may be performed each or both of between the first and second domains and between the third and fourth domains.

These domain sequences within the single-chain polypeptide can be selected and determined appropriately according to desired properties such as binding properties to a photocrosslinking group and to a target substance and the long-term stability of the present photocrosslinking group-recognizing complex protein.

Examples of the first domain include a first domain having three CDRs in each set of amino acid sequences of SEQ ID NOs: 1 to 3 and SEQ ID NOs: 4 to 6 or CDRs functionally equivalent thereto. The respective amino acid sequences correspond to antibody H chain CDR1, CDR2 and CDR3. The CDRs functionally equivalent have amino acid sequences derived from these amino acid sequences with the deletion, substitution or addition of one or several amino acids. These CDRs may be used without problems as long as the first domain having the CDRs can maintain binding properties to a photocrosslinking group. The respective CDRs may be combined appropriately in each set without problems as long as the first domain having the CDRs can maintain binding properties to a photocrosslinking group. These sequences may be used as the third domain.

Examples of the third domain include a third domain having three CDRs in each set of amino acid sequences of SEQ ID NOs: 7 to 9 and SEQ ID NOs: 10 to 12 or CDRs functionally equivalent thereto. The respective amino acid sequences correspond to antibody L chain CDR1, CDR2 and CDR3. The CDRs functionally equivalent have amino acid sequences derived from these amino acid sequences with the deletion, substitution or addition of one or several amino acids. These CDRs may be used without problems as long as the third domain having the CDRs can maintain binding properties to a photocrosslinking group. The respective CDRs may be combined appropriately in each set without problems as long as the third domain having the CDRs can maintain binding properties to a photocrosslinking group. These sequences may be used as the first domain.

The CDRs of the first and third domains may be used as these sets or combined appropriately between the domains as long as the first and third domains having the CDRs can maintain binding properties to a photocrosslinking group. The combination of the first and third domains can be combination of CDR sets derived from H and L chains.

The present invention also encompasses a nucleic acid encoding the photocrosslinking group-recognizing complex protein. The present invention further encompasses a construct including a nucleic acid serving as a gene vector. This construct for expressing the protein is used to transform a host cell (e.g., conventionally known *E. coli*-, yeast-, mouse- or human-derived cells for protein expression). As a result, the photocrosslinking group-recognizing complex protein can be expressed from the host cell.

Each domain of the photocrosslinking group-recognizing complex protein of the present invention, which can be expressed by the single expression vector, may be selected for design from the first to fourth domains. When plural domains of the photocrosslinking group-recognizing complex protein of the present invention are encoded by one expression vector, the domains can be expressed each individually as independent polypeptide chains. Alternatively, a vector may be constituted to express the protein as one polypeptide chain including the domains bound consecutively or via amino acids. The vector for expression of the photocrosslinking group-recognizing complex protein of the present invention can be designed and constructed by integrating constitutions necessary for transgene expression, such as known promoters, according to a host cell selected. The vector constitution can be constructed with reference to the constitutions such as known promoters according to a host cell selected. Alternatively, when *E. coli* is used as a host cell, the photocrosslinking group-recognizing complex protein, which is obtained as a foreign gene product, is immediately removed to the outside of the cytoplasm. This can reduce decomposition by protease. It is also known that even if this foreign gene product is toxic to the bacterial cell, its influence can be reduced by secreting the foreign gene product to the outside of the cell. Most known proteins secreted through a cytoplasmic membrane or inner membrane usually have a signal peptide at the N-terminus of their precursors. The precursors undergo the cleavage of the signal peptide by signal peptidase in the secretion process and become mature proteins. Most signal peptides have basic amino acids, hydrophobic amino acids and cleavage sites by signal peptidase located at the N-terminus thereof.

A nucleic acid encoding a conventionally known signal peptide (typically, pelB) can be arranged at the 5' end of the nucleic acid encoding the photocrosslinking group-recognizing complex protein of the present invention so as to secrete and express this protein. Alternatively, plural polypeptide chains including each domain or plural domains constituting the photocrosslinking group-recognizing complex protein may be inserted each independently into one vector. In this case, a nucleic acid encoding pelB can be arranged at the 5' end of a nucleic acid encoding each domain or polypeptide chain so as to promote the secretion thereof. To express a polypeptide chain including one or more domain(s), a nucleic acid encoding pelB can be arranged in the same way at the 5' end of the polypeptide chain so as to promote the secretion thereof. The photocrosslinking group-recognizing complex protein or the domain as a component thereof thus fused at the N-terminus with the signal peptide can be purified from the periplasmic fraction or medium supernatant. Considering convenient purification procedures for the expressed protein, a tag for purification may be arranged in a genetic engineering manner at the N- or C-terminus of a polypeptide chain formed by each independent domain or plural domains bound together. Examples of the tag for purification include a histidine tag comprising six consecutive histidine residues (hereinafter, referred to as His×6) and the glutathione-binding site of glutathione-S-transferase. Examples of a tag introduction method include: a method including inserting a nucleic acid encoding the purification tag into the 5' or 3' end of the nucleic acid encoding the photocrosslinking group-recognizing complex protein in the expression vector; and a method using a commercially available vector for purification tag introduction.

Hereinafter, a method for producing the photocrosslinking group-recognizing complex protein of the present invention by use of the expression vector will be described.

The photocrosslinking group-recognizing complex protein of the present invention or a polypeptide chain serving as a component thereof can be produced by transforming a conventionally known host cell for protein expression with the vector for expression of the photocrosslinking group-recognizing complex protein designed according to the host cell. In this case, the protein or the polypeptide chain serving as a component thereof is synthesized within the host cell by use of the protein synthesis system within the host cell. Then, the product of interest accumulated or secreted to the inside or outside of the host cell can be purified from the inside of the cell or cell culture supernatant to obtain the protein or the polypeptide chain serving as a component thereof. For example, when *E. coli* is used as a host cell, a nucleic acid encoding a conventionally known signal peptide (typically, pelB) is located at the 5' end of a nucleic acid encoding the photocrosslinking group-recognizing complex protein. The protein expressed therefrom can have a form easily secreted and expressed to the outside of the cytoplasm. When plural polypeptide chains for obtaining each domain constituting the photocrosslinking group-recognizing complex protein are expressed by one expression vector, a nucleic acid encoding pelB is arranged at the 5' end of a nucleic acid encoding each polypeptide chain. The secretion of the proteins to the outside of the cytoplasm can be promoted during their expression. Thus, the photocrosslinking group-recognizing complex protein thus fused at the N-terminus with the signal peptide can be purified from the periplasmic fraction or medium supernatant. The antibody fused with the His tag and GST as a purification tag can be purified by a purification method using a nickel chelate column and a glutathione-immobilized column, respectively. It is desired that procedures subsequent to protein expression induction should be conducted in a dark room or within the place surrounded by yellow curtains as much as possible.

The photocrosslinking group-recognizing complex protein of the present invention expressed within the bacterial cell may be obtained as insoluble granules. In this case, the bacterial cell obtained from the culture solution is disrupted by French press or ultrasonication. The insoluble granules can be obtained by centrifugation from the cell homogenate. The obtained insoluble granular fraction is solubilized with a buffer solution including a conventionally known denaturant containing urea and guanidine hydrochloride. Then, the solubilized fraction can be column-purified under denaturation conditions in the same way as above. The obtained column elution fraction can be subjected to refolding procedures for removing the denaturant and reconstructing active structure. The refolding method can be selected appropriately for use from conventionally known methods. Specifically, for example, a stepwise dialysis or dilution method may be used according to the protein of interest.

Plural domains or polypeptide chains of the photocrosslinking group-recognizing complex protein of the present invention may be expressed within the same host cell or separately in different host cells, combined and then converted into a complex formed thereby.

Furthermore, the protein may be expressed in vitro by the vector encoding the photocrosslinking group-recognizing complex protein of the present invention by use of a cell extract. Examples of the cell extract that can be used include *E. coli*, wheat germ and rabbit reticulocytes. However, the protein synthesis using a cell-free extract is generally performed under reduction conditions. Therefore, some treatment for forming a disulfide bond in the antibody fragment can be performed.

The dissociation constant ($K_D$) of the photocrosslinking group-recognizing complex protein of the present invention can be $10^{-4}$ M or less, particularly $10^{-6}$ M, to a photocrosslinking group.

One example of a method for obtaining such an antibody heavy chain variable region (VH) or light chain variable region (VL) having the ability to bind to a target substance according to the present invention can include a method described below.

First, a VH or VL gene library is prepared. These genes are comprehensively expressed as proteins. Next, proteins having binding properties to a target substance are selected according to their genes.

The gene library can be obtained from, for example, cord blood, tonsils, bone marrow, peripheral blood cells or spleen cells. For example, mRNA is extracted from human peripheral blood cells, and cDNA is synthesized from this mRNA. Next, a cDNA library of human VH or VL is prepared with a human VH- or VL-encoding sequence as a probe. For example, primers capable of extensively amplifying each of human VH families (VH1 to VH7) or primers capable of amplifying human VL are known in the art. RT-PCR using these primers appropriately combined for each of VH and VL is performed to obtain genes encoding VH and VL.

Alternatively, a phage display method may be used. In the phage display method, first, a gene library encoding VH, VL or a complex including these regions (e.g., Fab or scFv) is bound with a gene encoding a phage coat protein to prepare a phagemid library. Next, *E. coli* is transformed with the phagemid library. These genes are expressed as phages having a variety of VH or VL regions as a portion of the coat proteins. The phages can be used to select, in the same way as above, desired VH, VL or complex including these regions having binding properties to a target substance. The gene encoding VH or VL displayed as a fusion protein on the phage is encoded by the phagemid in the phage and can therefore be identified by DNA sequencing. Of course, a selection method equivalent to the phage display method can also be used.

Further more, the target substance-capturing protein (e.g., ankyrin or Affilin) having non-antibody structure having the ability to bind to a target substance according to the present invention can be selected with the selection method. Furthermore, a cell producing the antibody of interest is collected from an animal immunized with a target substance. The VH or VL nucleotide sequence and amino acid sequence can be identified with the same primers as above.

The second and fourth domains of the present invention can be designed based on the amino acid sequence of the variable region of a known antibody and antibody fragment against a target substance. When the antibody or antibody fragment against a target substance has not been obtained, an antibody against this target substance is first obtained. Then, the amino acid sequence of the antibody is analyzed. The domains can also be designed based on this amino acid sequence. Both the third and fourth domains may constitute the photocrosslinking group-recognizing complex protein of the present invention. The nucleotide sequence of the VH or VL thus obtained can be used to prepare the photocrosslinking group-recognizing complex protein of the present invention.

Object to be Bound Having Photocrosslinking Group

An object to be bound that can be utilized for selecting the photocrosslinking group-recognizing complex protein by immunization or panning is exemplified by those described above for the anti-photocrosslinking group antibody.

Substrate and Structure

The photocrosslinking group-recognizing complex protein of the present invention can be combined with a substrate to obtain a structure. This structure can be utilized in a variety of applications. The substrate that can be utilized for this purpose is exemplified by those described above for the anti-photocrosslinking group antibody.

Target Substance

The photocrosslinking group-recognizing complex protein of the present invention is constituted to include a domain having binding properties to a photocrosslinking group and a domain having binding properties to a target substance. As a result, this protein can be utilized as a complex protein for detecting a target substance. Any molecule can be used as this target substance to be detected as long as this molecule is a substance that can serve as an antigen by each approach using antigen-antibody reaction. For example, the target substances are broadly classified into non-biological materials and biological materials.

The non-biological materials, biological materials or specific proteins that can be used as target substances in the present invention are exemplified those disclosed in the paragraphs 0108 to 0111 of Japanese Patent Application Laid-Open No. 2005-312446. More specifically, examples of the non-biological materials include PCBs as environmental pollutants differing in the number and position of chlorine substitution, dioxins also differing in the number and position of chlorine substitution, and endocrine disrupting chemicals called so-called environmental hormones. Examples of the biological materials include biological materials selected from nucleic acids, proteins, sugar chains, lipids and complexes thereof. Examples of the proteins include disease markers. Of course, the target substance is not limited to these substances.

Kit for Detecting Target Substance

The photocrosslinking group-recognizing complex protein of the present invention can be used to constitute a kit for detecting a target substance. For example, a photocrosslinking group-recognizing complex protein is used in which an antibody and a variant thereof that specifically binds to a target substance is used in the second domain and in the fourth domain optionally used. The kit for detecting a target substance can include this photocrosslinking group-recognizing complex protein, a substrate having a photocrosslinking group on the surface, and an optional detection unit for detecting the target substance immobilized via the photocrosslinking group-recognizing complex protein on the substrate. For example, when a gold substrate having a photocrosslinking group on the surface is used as a substrate, the target substance immobilized via the photocrosslinking group-recognizing complex protein on the substrate including a photocrosslinking group may be detected by measurement using the surface plasmon resonance measurement apparatus.

EXAMPLES

Hereinafter, the present invention will be described more specifically with reference to Examples. However, the scope of the present invention is not limited to Examples below. In Examples shown below, procedures other than the step of photocrosslinking a protein of the present invention through light irradiation can be conducted basically in a dark room or within the place surrounded by yellow curtains.

Example 1

Mouse Immunization with Immunogen

To acquire an anti-photocrosslinking group antibody of the present invention, a mouse was immunized six times with a 4-(1-Azi-2,2,2-trifluoroethyl)benzoic acid-KHL conjugate (manufactured by Yanaihara Institute Inc.) as an immunogen. The immunogen solution before immunization was handled within the place surrounded by yellow curtains.

The first immunization was performed by the following procedures; first, 0.7 ml of Freund's complete adjuvant (manufactured by CALBIOCHEM, Code No. 344289) was added to 0.7 ml of a 2 mg/ml immunogen solution (1.4 mg of immunogen). This mixture was mixed for approximately 10 minutes in syringe barrels connected via a joint to prepare an emulsion. Next, mice (Balb/c, female, seven-week-old) were intraperitoneally immunized with 0.2 ml (0.2 mg) of this emulsion per mouse. Five mice in total were immunized in this manner.

The second to sixth immunizations were performed by the following procedures: first, 0.7 ml of Freund's incomplete adjuvant (manufactured by DIFCO, Code No. 263910) was added to 0.7 ml of a 1 mg/ml immunogen solution (0.7 mg of immunogen). This mixture was mixed for approximately 10 minutes in syringe barrels connected via a joint to prepare an emulsion. Next, the mice were intraperitoneally immunized with 0.2 ml (0.1 mg) of this emulsion per mouse. Antisera were obtained by partial blood collection on the 12th day after the fourth immunization and on the 7th day after the fifth immunization and used in antibody titer measurement.

Example 2

Antibody Titer Measurement of Antisera

The antibody titers of the partial blood collection samples of Example 1 were measured by conventionally known ELISA according to different methods (1) and (2) described below. All the procedures shown below were conducted in the dark as much as possible.

(1) Measurement Method Using Immobilization of Goat Anti-mouse IgG (Fc) Antibody An antigen sample used was 4-(1-Azi-2,2,2-trifluoroethyl) benzoyl-Arg-Arg-NHNH-biotin (manufactured by Yanaihara Institute Inc.). The following components were added to each well of a goat anti-mouse IgG (Fc) antibody-immobilized, 96-well microtiter plate: (1) 50 μl of an antigen sample solution diluted to 0.01 ng/ml to 10 μg/ml; and (2) 50 μl of antiserum (each antiserum obtained by partial blood collection after the fourth and fifth immunizations) diluted 2000 to 1600 folds.

In this state, the reaction was allowed to proceed at room temperature for 3 hours. Next, the 96-well titer plate was washed. Then, an SA-HRP solution (manufactured by ONCOGENE, Cat No. OR03L) diluted 3000 folds was dispensed at a concentration of 100 μl/well. The reaction was allowed to proceed at room temperature for 2 hours. The plate was further washed. Then, a substrate solution (OPD; manufactured by SIGMA, Cat No. UK-B25) was dispensed at a concentration of 100 μl/well. The reaction was allowed to proceed at room temperature for 20 minutes. Finally, the reaction was terminated by the addition of 100 μl of a 2 N sulfuric acid solution. Absorption at OD 492 nm was measured with a microplate reader.

FIGS. 9A, 9C, 9E, 9G and 9I illustrate the results of antibody titer measurement using the antisera (labeled with biotin) of mouse No. 1 to 5 obtained by partial blood collection after the fourth immunization. Alternatively, FIGS. 9B, 9D, 9F, 9H and 9J illustrate the results of antibody titer measurement using the antisera (labeled with biotin) of mouse No. 1 to 5 obtained by partial blood collection after the fifth immunization. When the antisera obtained by partial blood collection after the fourth and fifth immunizations were compared, all the mice had almost the same antibody titer. Mouse No. 3 exhibited the highest antibody titer, followed by No. 2, No. 4, No. 1 and No. 5 in this order. In FIGS. 9A to 9L, the line -●- denotes ×2000, the line -■- denotes ×4000, the line -▲- denotes ×8000, and the line -○- denotes ×6000.

(2) Measurement Method Using Immobilization of Antigen

An antigen sample used was a 4-(1-Azi-2,2,2-trifluoroethyl)benzoic acid-BSA conjugate (manufactured by Yanaihara Institute Inc.). First, a 0.1 M NaHCO$_3$ solution was used to prepare a 1 μg/ml antigen sample solution. This antigen sample solution was added at a concentration of 0.1 ml/well to a 96-well microtiter plate and left standing overnight at 4° C. The solution was discarded. Block Ace (diluted 4 folds) was dispensed at a concentration of 0.3 ml/well and further left standing overnight at 4° C. The solution in the plate was removed. The plate was dried for 2 days in a desiccator to prepare an antigen sample-immobilized, 96-well microtiter plate. This plate was stored at 4° C. until use. The antiserum (each antiserum obtained by partial blood collection after the fourth and fifth immunization) diluted 3000 to 375000 folds was added at a concentration of 100 µl/well to the plate. The reaction was allowed to proceed at room temperature for 3 hours. Next, the 96-well titer plate was washed. Then, a goat anti-mouse antibody-HRP conjugate solution (manufactured by ICN, Code No. 674281) diluted 10000 folds was dispensed at a concentration of 100 µl/well. The reaction was allowed to proceed at room temperature for 2 hours. The plate was further washed. Then, a substrate solution (OPD; manufactured by SIGMA, Cat No. UK-B25) was dispensed at a concentration of 100 µl/well. The reaction was allowed to proceed at room temperature for 20 minutes. Finally, the reaction was terminated by the addition of 100 µl of a 2 N sulfuric acid solution. Absorption at OD 492 nm was measured with a microplate reader.

Figure 9A:
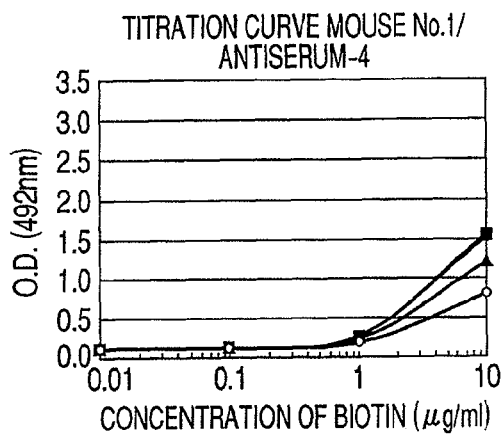
FIGS. 9A, 9B, 9C, 9D, 9E, 9F, 9G, 9H, 9I, 9J, 9K and 9L are respectively a diagram illustrating results obtained in Example 2.
Figure 9B:
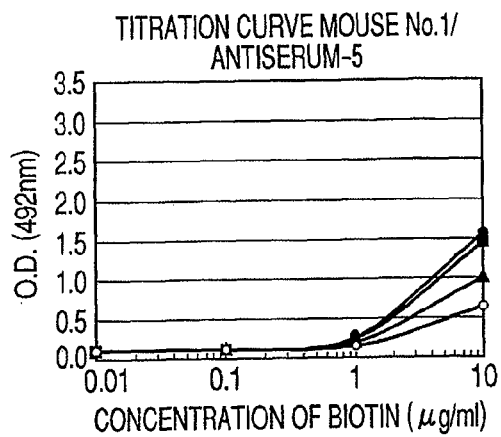
Figure 9C:
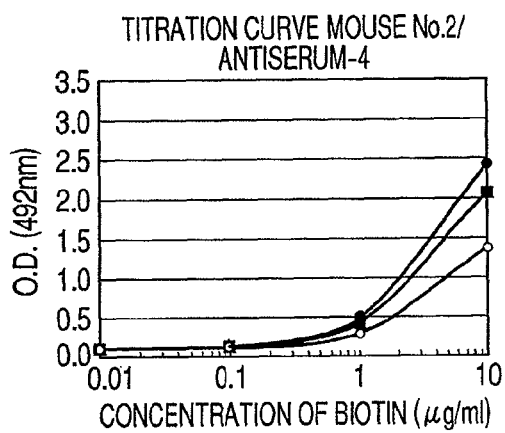
Figure 9D:
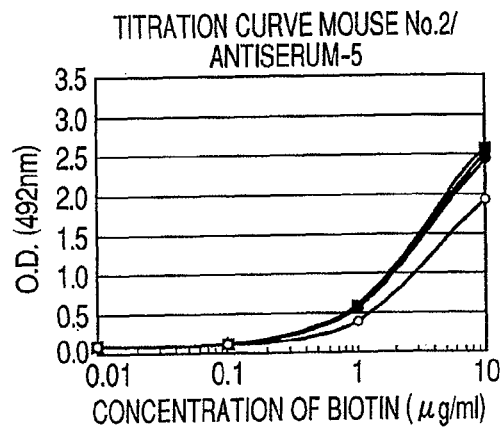
Figure 9E:
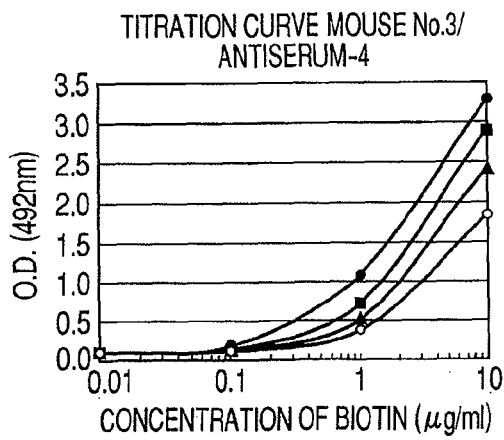
Figure 9F:
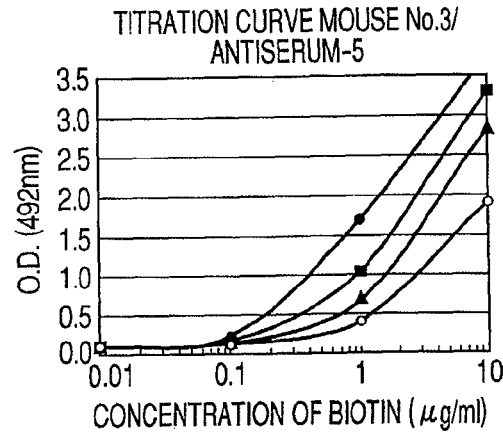
Figure 9G:
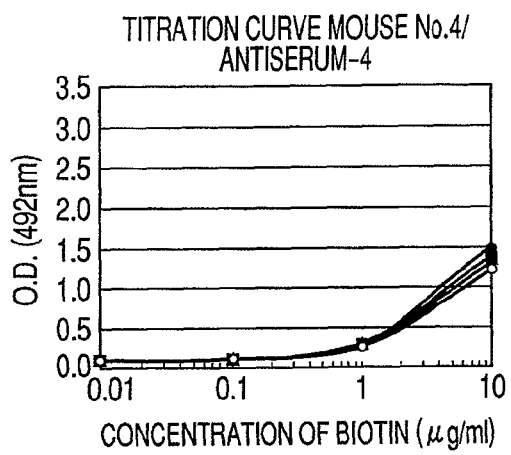
Figure 9H:
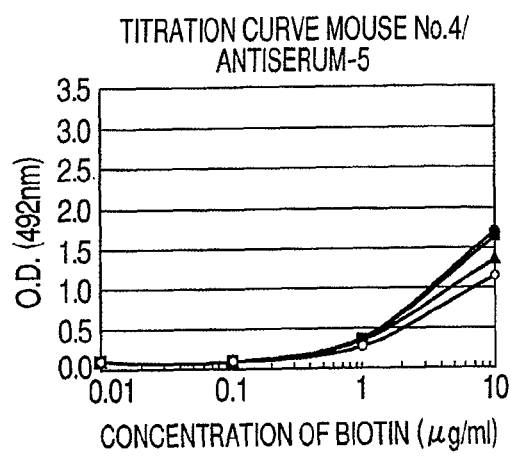
Figure 9I:
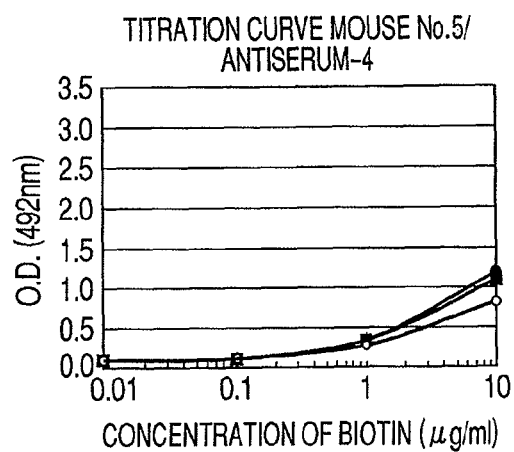
Figure 9J:
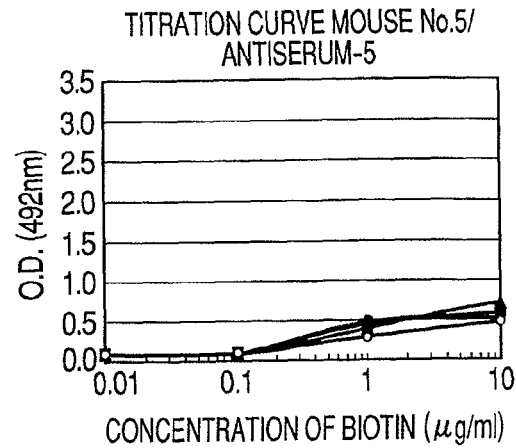
Figures 9K, 9L:
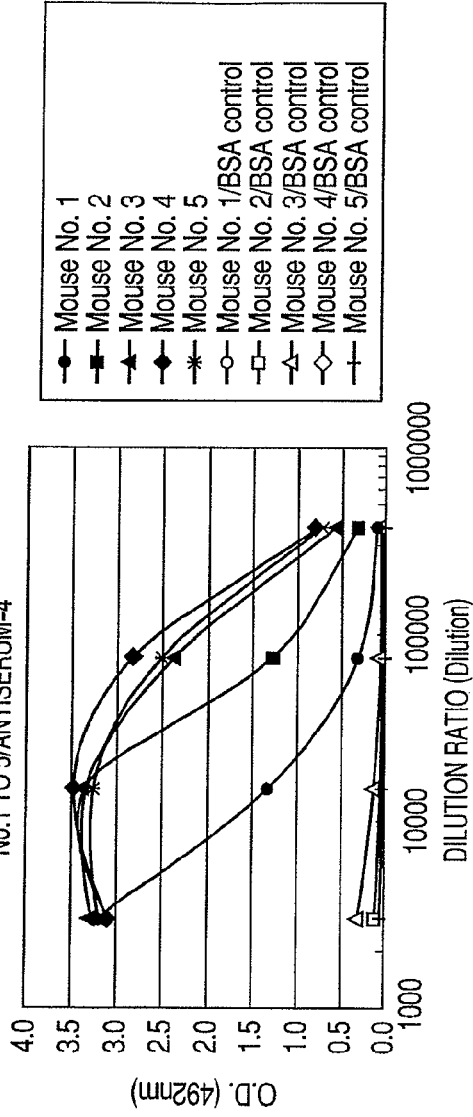
Figure 10A:
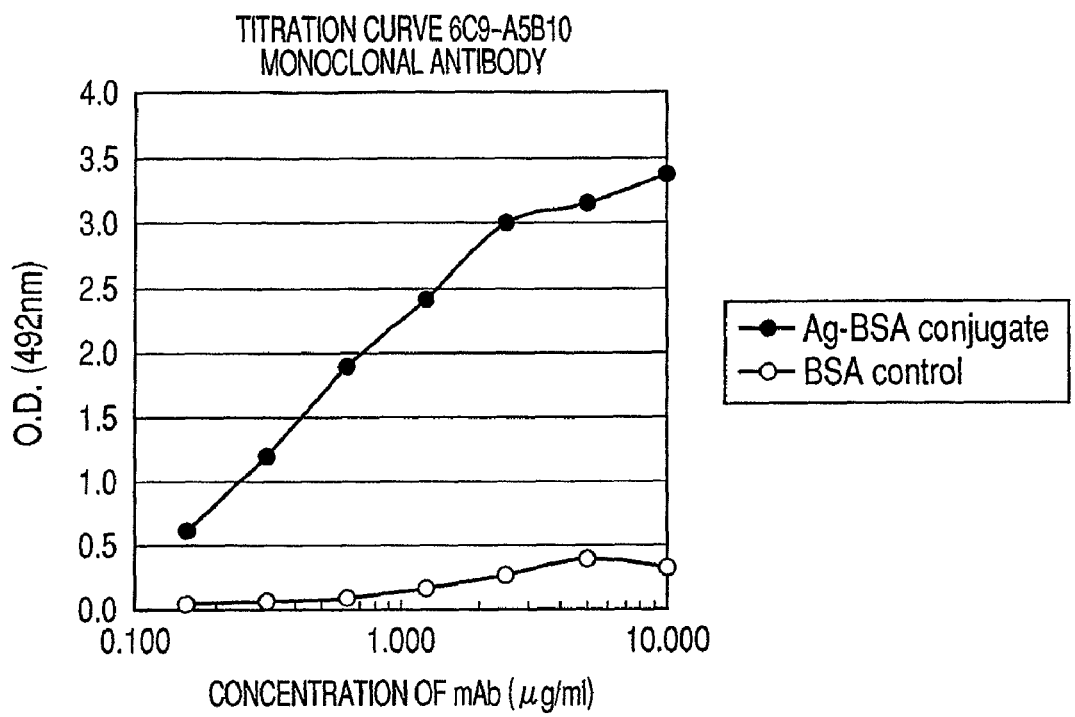
FIGS. 10A, 10B, 10C, 10D, 10E and 10F are respectively a diagram illustrating results obtained in Example 8.
Figure 10B:
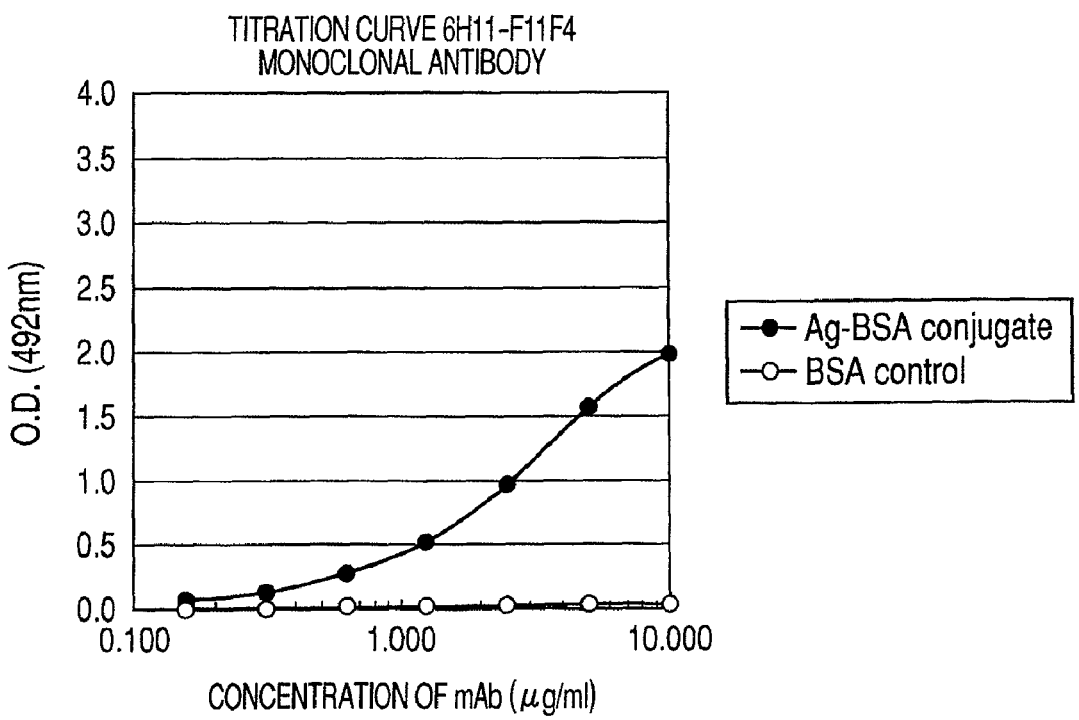
Figure 10C:
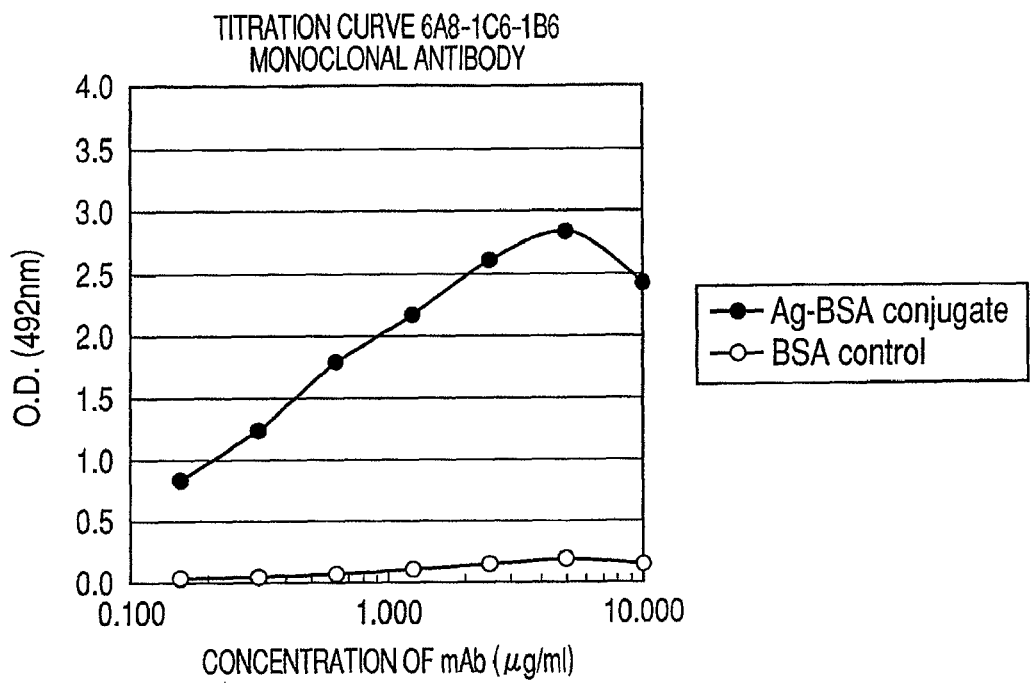
Figure 10D:
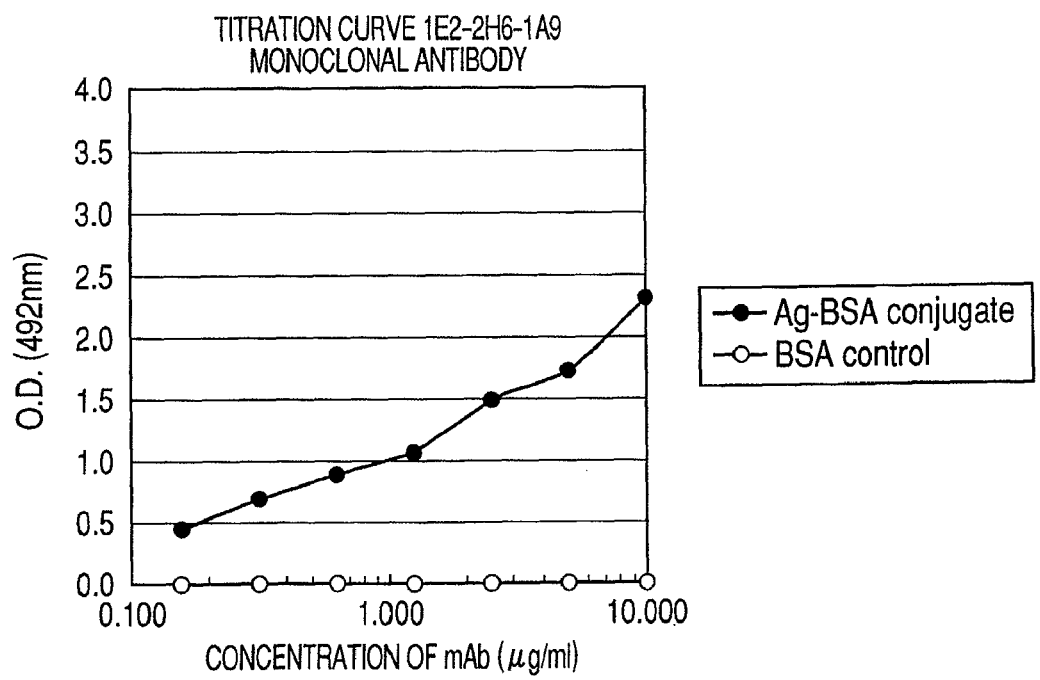
Figure 10E:
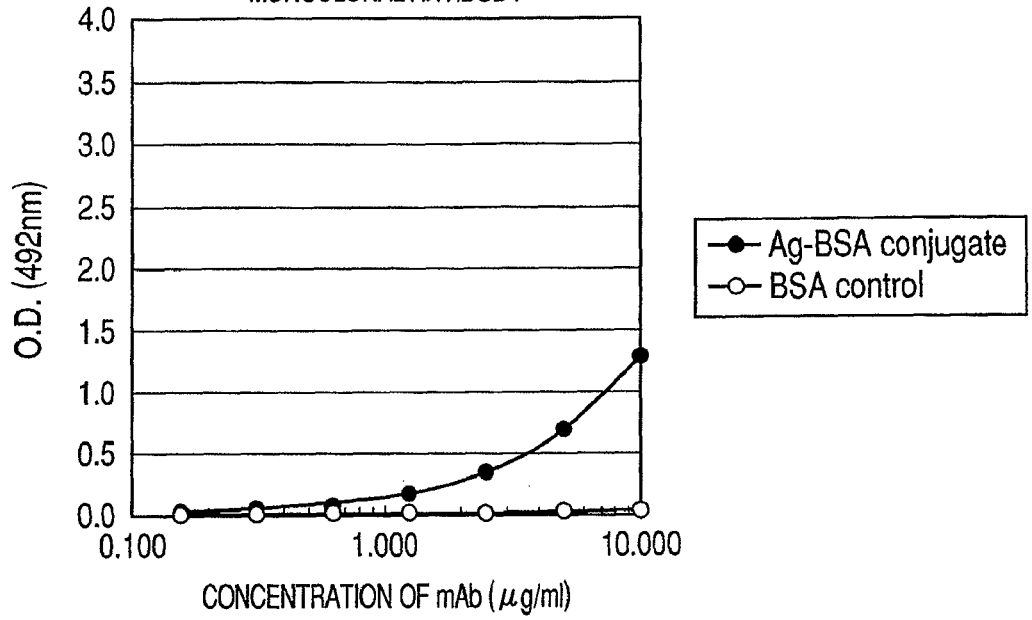
Figure 10F:
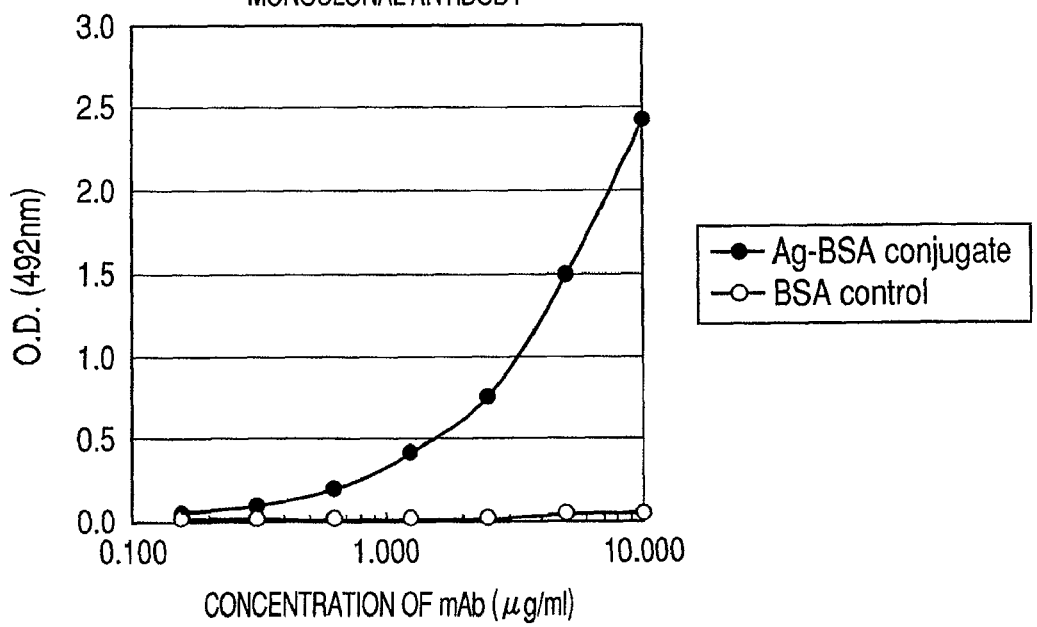

FIG. 9K illustrates the results of antibody titer measurement using the BSA conjugate-immobilized plate of the antisera of mouse No. 1 to 5 obtained by partial blood collection after the fourth immunization. FIG. 9L illustrates the results of antibody titer measurement using the BSA conjugate-immobilized plate of the antisera of mouse No. 1 to 5 obtained by partial blood collection after the fifth immunization. All the mouse antisera were hardly reactive with a BSA control plate. When the antisera obtained by partial blood collection after the fourth and fifth immunizations were compared, all the mice had almost the same antibody titer. Mouse No. 5 exhibited the highest antibody titer, followed by No. 4, No. 3, No. 2 and No. 1 in this order.

Example 3

Hybridoma Preparation (Cell Fusion)

Based on the results of antibody titer measurement after partial blood collection of Example 2, mouse No. 3 and No. 5 were used as samples for hybridoma preparation. First, 5 ml of a culture solution (RPMI 1640; manufactured by ICN) was added to a 5-cm Petri dish. A flame-sterilized steel mesh was further added thereto. The spleen excised from the mice was crushed by hands above the mesh to obtain isolated spleen cells. The spleen cells were transferred to a 50-ml centrifuge tube and washed twice with 20 ml of a culture solution. P3U1 myeloma cells cultured in advance were washed twice with 20 ml of a culture solution. The numbers of the spleen and myeloma cells were separately counted. These spleen and myeloma cells were mixed at a 10:1 ratio and centrifuged. To the cell pellets, 2 ml of a PEG solution HYBRI-MAX (manufactured by SIGMA) was added over 30 seconds. Then, the mixture was slowly mixed for 30 seconds. To the mixture, 5 ml of a culture solution was added over 2 minutes. Additional 5 ml of a culture solution was added thereto. Then, the mixture was incubated at 37° C. for 3 minutes and then centrifuged at 800 rpm for 5 minutes. An HAT medium (manufactured by Invitrogen) was gradually added to the cell pellets to adjust the number of the spleen cells to 2 to $3 \times 10^5$ cells/0.2 ml/well. Then, this mixture was further dispensed at a concentration of 0.2 ml/well to a 96-well culture plate. Then, the mixture was cultured for 10 days in a $CO_2$ incubator to complete cell fusion.

Example 4

Screening and Antibody Titer Measurement

The hybridomas obtained in Example 3 were measured in the same way as in the antibody titer measurement method described in Example 2(2). At the point in time when an increase in antibody titer was confirmed, the screening of the hybridomas was completed. Secondary screening was conducted to obtain hybridoma cells with a high antibody titer. As a result, six hybridoma strains in total of two strains from mouse No. 3 and four strains from mouse No. 5 were obtained which produced an antibody reactive with a 4-(1-Azi-2,2,2-trifluoroethyl)benzoic acid-BSA conjugate-immobilized plate. These six hybridoma strains obtained were designated as 6H11-F11F4, 6C9-A5B10, 6A8-1C6-1B6, 1E2-2H6-1A9, 4G2-1E10-1F10 and 3E12-1B6-1A5.

Example 5

Cloning (Twice) and Ascitic Fluid Preparation

The mouse thymus was excised, and thymus cells were prepared therefrom. The thymus cells were adjusted to $5 \times 10^6$ cells/ml with a culture solution. A 100 µl aliquot thereof was added to each well of a 96-well culture plate. The hybridoma cells selected by secondary screening of Example 4 were separately diluted to 10 cells/ml with a culture solution. A 100 µl aliquot each of the diluted cell solutions was added to each well of the prepared culture plate. After 10-day culture, a colony in each well was observed. Wells having only one colony were confirmed. Next, the culture supernatants were collected. Positive wells were selected in decreasing order of OD values by the antibody titer measurement method. Approximately $5 \times 10^6$ clone cells derived from each hybridoma were added to each of two nude mice to which 0.5 ml of pristane was intraperitoneally administered in advance. After approximately 10 days, ascitic fluids were collected from the mice.

Example 6

Monoclonal Antibody Purification

The ascitic fluids obtained in Example 5 were subjected to degreasing treatment. An equal amount of ammonium sulfate was gradually added dropwise thereto and then left standing at 4° C. for 1 hour. The suspensions were centrifuged at 3500 rpm for 30 minutes. After the removal of the supernatants, the pellets were dissolved in the same amount of Dulbecco's PBS (−) (NISSUI PHARMACEUTICAL CO., LTD.) as the original ascitic fluid amount. The solutions were dialyzed against a saline (5 L×2) and cryopreserved at −30° C. A monoclonal antibody obtained from each hybridoma in Example 5 was designated the same name as the name of the original hybridoma strain. Table 1 shows the amounts of the respective ascitic fluids collected and the amounts of the respective antibodies purified.

TABLE 1

| | Monoclonal antibody | | |
|---|---|---|---|
| Antibody name | Isotype | Amount of ascitic fluid | Amount of antibody purified |
| 6H11-F11F4 | IgM(k) | 15 ml | 29.0 mg |
| 6C9-A5B10 | IgM(k) | 9.4 ml | 37.5 mg |
| 6A8-1C6-1B6 | IgM(k) | 12.5 ml | 124.0 mg |
| 1E2-2H6-1A9 | IgM(k) | 13.0 ml | 66.0 mg |
| 4G2-1E10-1F10 | IgM(k) | 10.5 ml | 12.9 mg |
| 3E12-1B6-1A5 | IgM(λ) | 11.3 ml | 9.0 mg |

Example 7

Isotype Determination of Monoclonal Antibody

The isotypes of the purified monoclonal antibodies were determined with Mouse Antibody Isotyping Kit (Dainippon Pharmaceutical Co., Ltd.; Code No. MMT1). To a tube included in the kit, 150 µl of a culture solution was added and left standing for 30 seconds. Then, the solution was stirred. A stick included in the kit was added to the tube. The reaction was allowed to proceed. Each antibody isotype is summarized in Table 1. All the obtained monoclonal antibodies belonged to IgM class. Specifically, the antibody 3E12-1B6-1A5 was IgM(λ), and the remaining antibodies 6H11-F11F4, 6C9-A5B10, 6A8-1C$_6$-1B6, 1E2-2H6-1A9 and 4G2-1E10-1F10 were IgM(κ).

Example 8

Reactivity of Purified Monoclonal Antibody

The reactivity of the antibodies was evaluated in the same way as in the antibody titer measurement method described in Example 2(2). Dilution series of concentrations were prepared for the six purified monoclonal antibodies obtained in Example 6 instead of the antisera of Example 2. These dilution series were subjected to measurement. As a result, it was demonstrated as illustrated in FIGS. 10A to 10F that all of these six monoclonal antibodies were hardly reactive with a BSA control plate (○) and were significantly reactive in a concentration-dependent manner with an antigen-displaying BSA plate (●).

Example 9

Gene Sequencing of Antibody Variable Region (1) Total RNA Preparation

Of the six hybridoma cells obtained in Example 4, three (1E2-2H6-1A9, 6A8-1C6-1B6 and 6C9-A5B10) monoclonal antibodies were subjected to gene analysis. In Examples below, these three monoclonal antibodies produced were newly designated as PM1, PM2 and PM3 in this order. The hybridoma cells collected and treated were disrupted by homogenization in a Trizol reagent (manufactured by Invitrogen). Subsequent procedures were conducted under conditions according to the protocol of the Trizol reagent to extract and purify Total RNAs. The total RNAs were treated with DNase I (Takara Bio) for decomposing the residual DNAs and then purified.

(2) RT-PCR Reaction

The total RNAs prepared in the preceding paragraph (1) were used as templates to perform RT-PCR reaction. High Fidelity RNA PCR Kit (Takara Bio) and TaKaRa Ex Taq (Takara Bio) were used in RT reaction and in PCR, respectively. Primers for each H or L chain amplification used in RT reaction were a primer set (Light Primer Mix (Amersham 27-1583-01) and Heavy Primers (Amersham 27-1586-01)) included in Mouse scFv Module Recombinant Phage Antibody system (Amersham Biosciences). Reaction composition and reaction conditions are shown below.

| <Composition of RT reaction solution> | |
|---|---|
| 2 × Bca 1st Buffer | 10.0 |
| 25 mM MgSO$_4$ | 4.0 |
| dNTP Mixture | 1.0 |
| RNase Inhibitor | 0.5 |
| Bca PLUS RTase | 1.0 |
| Oligo dT-Adaptor Primer FB | 1.0 |
| RNA | 1.0 |
| RNase Free H$_2$O | Up to 20.0 µl |

| <RT reaction conditions> | |
|---|---|
| 65° C. | 1 min. |
| 30° C. | 1 min. |
| 30 → 65° C. | 15 min. (30° C. → 65° C. over 15 min.) |
| 65° C. | 30 min. |
| 98° C. | 5 min. |
| 5° C. | 5 min. |

| <Composition of PCR reaction solution> | |
|---|---|
| 10 × Ex Taq Buffer | 2.0 |
| 2.5 mM dNTPs | 1.6 |
| Primer(*) | |
| RT Product | 1.0 |
| Ex Taq (5 U/µl) | 0.1 |
| RNase Free H$_2$O | Up to 20.0 µl |

(*)For L chain amplification, 0.8 µl of Light Primer Mix (Amersham Biosciences) was added.

For H chain amplification, 0.4 µl each of Heavy Primers 1 and 2 (Amersham Biosciences) was added.

| <PCR reaction conditions> | |
|---|---|
| 96° C. | 5 min. |
| 94° C. 30 sec. → 55° C. 30 sec. → 72° C. 1 min., 30 cycles | |
| 72° C. | 5 min. |
| 4° C. | |

All the cDNA-derived amplifications of the RT-PCR reaction solutions were confirmed by 1% agarose electrophoresis.

(3) TA Cloning

Each amplification product obtained by RT-PCR reaction was excised from the gel and purified by removing the primers by use of MinElute Gel Extract Kit (Qiagen). The purified products were subjected to ligation reaction with pT7 Blue-T vectors (Takara Bio) by use of DNA Ligation Kit v2.1 (Takara Bio). Then, E. coli DH5α strains (Takara Bio) were transformed with the ligation products. The obtained white colonies were subjected to colony PCR using the primers (M13-47 and RV-M (Takara Bio)) on the vectors. Eight clones from each colony for which an amplification product with a putative molecular weight was confirmed were used in sequencing.

(4) Sequencing

Plasmid DNAs were prepared from the selected clones and subjected to sequencing using M13-47 and RV-M primers. BigDye Terminator v1.1 Cycle Sequencing Kit (Applied Biosystems) was used in sequencing reaction. The reaction was performed under conditions according to the protocol included in the kit. The sequencing reaction products were purified by gel filtration using Sephadex G50 Fine. The purified products were analyzed by electrophoresis using ABI PRISM3100 to determine the nucleotide sequence of each antibody variable region (VH and VL) of the monoclonal antibodies (PM1 and PM2) produced by two hybridomas (PM1-VH: SEQ ID NO: 13, PM1-VL: SEQ ID NO: 14, PM2-VH: SEQ ID NO: 15 and PM2-VL: SEQ ID NO: 16).

Example 10

Deposition of Cell

The hybridomas that produce the PM1, PM2 and PM3 monoclonal antibodies were deposited with International Patent Organism Depositary as accession Nos. FERM P-20855 (FERM BP-10762), FERM P-20856 (FERM BP-10763) and FERM P-20857 (FERM BP-10764), respectively. The hybridomas that produce 4G2-1E10-1F10 and 6H11-F11F4 were deposited with International Patent Organism Depositary as accession Nos. FERM BP-10825 and FERM BP-10826, respectively.

Further we expect that photocrosslinking effect evaluation of purified antibody, acquisition of photocrosslinking group- and HEL-recognizing complex protein, expression vector preparation, protein expression and purification, immobilization of photocrosslinking group- and HEL-recognizing complex protein onto QCM gold substrate by photocrosslinking and HEL binding evaluation using QCM can be performed as described in the following examples.

Example 11

Photocrosslinking Effect Evaluation of Purified Antibody

Figure 11:
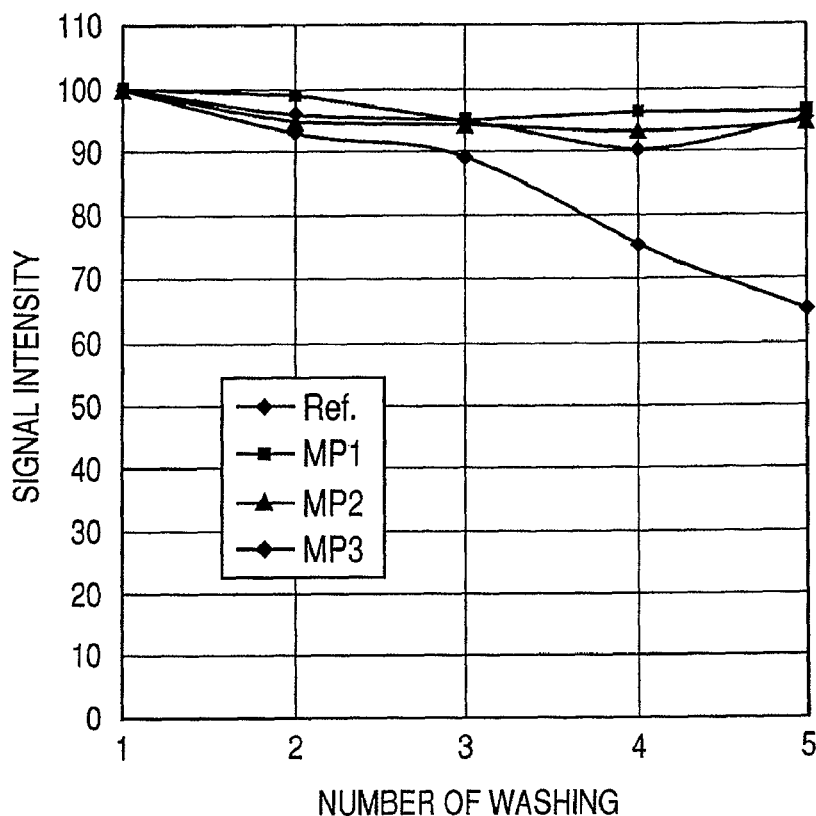
FIG. 11 is a diagram illustrating results obtained in Example 11.

The monoclonal antibodies (PM1, PM2 and PM3) purified in Example 6 are separately dispensed to a plate in which an antigen sample prepared in the same way as in the antibody titer measurement method described in Example 2(2) was immobilized. The antigen sample used is a 4-(1-Azi-2,2,2-trifluoroethyl)benzoic acid-BSA conjugate. After dispensing, the reaction is allowed to proceed at room temperature for 3 hours. Next, the 96-well titer plate is washed. Then, the plate is irradiated with a light with a wavelength of 365 nm at approximately 20 mW/cm$^2$ in a UV crosslinker CL-1000L (Funakoshi Corp.). Then, washing and light irradiation are repeated four times. A goat anti-mouse antibody-HRP conjugate solution (manufactured by ICN, Code No. 674281) diluted 10000 folds is further dispensed at a concentration of 100 µl/well to the plate at each step. After dispensing, the reaction is allowed to proceed at room temperature for 2 hours. The plate is further washed. Then, a substrate solution (OPD; manufactured by SIGMA, Cat No. UK-B25) is dispensed at a concentration of 100 µl/well. The reaction is allowed to proceed at room temperature for 20 minutes. Finally, the reaction is terminated by the addition of 100 µl of 2 N sulfuric acid solution. Absorption at OD 492 nm is measured with a microplate reader. A plate washed at the same times without light irradiation is prepared as a control experiment. As a result, almost 100% of all the monoclonal antibodies PM1 to PM3 are held by the plate irradiated with light, whereas these antibodies are observed to fall off the control plate without light irradiation due to washing (FIG. 11).

Example 12

Acquisition of Photocrosslinking Group- and HEL-Recognizing Complex Protein)

(1) Preparation of Nucleic Acid Fragment Encoding Anti-Photocrosslinking Group Antibody Variable region VH NcoI and NheI restriction sites are arranged at the 5' and 3' ends of the anti-photocrosslinking group antibody variable region VH (PM2-VH; SEQ ID NO: 15), respectively, to prepare an anti-photocrosslinking group antibody variable region VH (hereinafter, referred to as VHp) for introduction into a vector. Primers for this purpose are prepared as follows:

```
PM2-VH-F (SEQ ID NO: 17):
5'-NNNNNCCATGGCCCAGGTGCAGCTGCAGGAGCTGGG-3'

PM2-VH-B (SEQ ID NO: 13):
5'-NNNNNGCTAGCTGAGGAGACGGTGACCGTGG-3'
```

PCR is performed with the primer set and a commercially available PCR kit according to the formulation recommended by the manufacturer to obtain a base pair of approximately 350 bp. Big Dye-PCR reaction is performed with the VHB-F and a commercially available sequencing reaction kit according to the composition of the reaction solution. The temperature cycle is set to 96° C.×3 min.→(94° C.×1 min.→50° C.×1 min.→68° C.×4 min.)×30 cycles→4° C. The fragment having the VH-encoding nucleotide sequence of interest is confirmed to be obtained.

(2) Preparation of Nucleic Acid Fragment Encoding Anti-photocrosslinking Group Antibody Variable Region VL An NheI restriction site and a linker (GGGGS)-encoding nucleic acid are arranged at the 5' end of the anti-photocrosslinking group antibody variable region VL (PM2-VL; SEQ ID NO: 16), and an SacII restriction site upstream of His×6 was arranged at the 3' end thereof to prepare an anti-photocrosslinking group antibody variable region VL (hereinafter, referred to as VLp) for introduction into a vector. Primers for this purpose are prepared as follows:

```
PM2-VL-F (SEQ ID NO: 19):
5'-NNNNNGCTAGCGGTGGCGGTGGCTCTGATATCGTCCTGACCCAGAGC-3'

PM2-VL-B (SEQ ID NO: 20):
5'-NNNNNCCGCGGATTTCAGCTCCAGCTTGGTCC-3'
```

A nucleic acid fragment is obtained in the same way as the preceding paragraph (1) except that these primers are used. The nucleic acid fragment is confirmed to have the VL nucleotide sequence of interest.

Example 13

Expression Vector Preparation

These two nucleic acid fragments are used to construct two expression vectors according to constitution below.

(1) Preparation of Vector for VHp-VLh Expression (pPHEL)
(i) Insertion of VHp

A vector pGHEL (gold-binding VH-HyHEL10-recognizing VL) disclosed in Japanese Patent Application Laid-Open No. 2005-312446 is cleaved with restriction enzymes NcoI/

NheI (both, New England Biolabs). The obtained fragment mixture is treated with a spin column 400HR (Amersham Biosciences). Next, the PCR product (VHp) amplified in Example 12 is also cleaved with restriction enzymes NcoI/NheI. The obtained cleaved fragment is purified with a commercially available gel purification kit (SV Gel and PCR Clean-up system; Promega). These two fragments are ligated by use of a commercially available T4 ligase kit (Roche) formulated by the method recommended by the manufacturer. The ligation solution is used to transform 40 μL of JM109 competent cells (Promega) by a heat shock method. Then, the transformed cells are seeded onto an LB/ampicillin (amp.) plate and left standing overnight at 37° C. Next, arbitrary colonies in the plate are transferred and seeded onto 3 mL of LB/amp. liquid medium and shake-cultured overnight at 37° C. Then, a plasmid is collected with a commercially available MiniPreps kit (Plus Minipreps DNA Purification System; Promega). The nucleotide sequence of the obtained plasmid is confirmed by the sequencing method using MP1-VH-F and -B. As a result, the insertion of the fragment of interest is confirmed. Consequently, an anti-photocrosslinking group antibody variable region VH-HyHEL10-recognizing VL construct is obtained.

(2) Preparation of Vector for VHh-VLp Expression (pH-PHOTO)

(ii) Insertion of VLp

A vector pHGOLD (HyHEL10-recognizing VH-gold-binding VL) disclosed in Japanese Patent Application Laid-Open No. 2005-312446 is cleaved with restriction enzymes NheI/SacII (both, New England Biolabs). The obtained fragment mixture is treated with a spin column 400HR (Amersham Biosciences). Next, the PCR product (VLp) amplified in Example 12 is also cleaved with restriction enzymes NheI/SacII. The obtained cleaved fragment is purified with a commercially available gel purification kit (SV Gel and PCR Clean-up system; Promega). These two fragments are ligated by use of a commercially available T4 ligase kit (Roche) formulated by the method recommended by the manufacturer. After ligation, transformation is performed in the same way as above. The obtained plasmid is confirmed in the same way as in the preceding paragraph (1) to be the vector pHPHOTO for VHh-VLp expression of interest (Primers for confirmation: MP1-VL-F and -B).

Example 14

Protein Expression and Purification

The expression vectors for expressing polypeptides of the VHp-VLh obtained in Example 13(i) and the VHh-VLp obtained in Example 13(ii) are used to perform protein expression and purification steps described below in individual systems. Thus, the polypeptide chains VHp-VLh and VHh-VLp are obtained respectively. Procedures after the completion of refolding shown below are performed in the dark place or within the place surrounded by yellow curtains.

1) Transformation

These two expression vectors are separately used to transform 40 μL of BL21 (DE3) competent cell solution. The transformation is performed under conditions involving heat shock on ice→42° C.×90 sec.→on ice. Each BL21 solution transformed by heat shock is shake-cultured at 37° C. for 1 hour after the addition of 750 μL of LB medium. Then, the solution is centrifuged at 6000 rpm×5 min. A 650 μL aliquot of the culture supernatant is discarded. The remaining culture supernatant and the precipitated cell fraction are stirred, and the mixture is then seeded onto an LB/amp. plate and left standing overnight at 37° C.

2) Preliminary Culture

Colonies on the plate are randomly selected and shake-cultured overnight at 28° C. in 3.0 mL of LB/amp. medium.

3) Main Culture

The preliminary culture solution is transferred and seeded onto 750 mL of 2×YT medium. The culture is further continued at 28° C. At the point in time OD 600 exceeded 0.8, IPTG is added at a final concentration of 1 mM thereto. The solution is further cultured overnight at 28° C.

4) Purification

The polypeptide chains of interest are purified from insoluble granular fractions by steps shown below.

(i) Collection of Insoluble Granules

Each culture solution obtained in the preceding paragraph 3) is centrifuged at 6000 rpm×30 min. to obtain a pellet as a bacterial cell fraction. The obtained bacterial cells are suspended in 15 ml of Tris solution (20 mM Tris/500 mM NaCl) on ice. The obtained suspension is disrupted by French press to obtain a bacterial cell homogenate. Next, the bacterial cell homogenate is centrifuged at 12000 rpm×15 min. The supernatant is removed to obtain a pellet as an insoluble granular fraction.

(ii) Solubilization of Insoluble Granular Fraction

The insoluble fraction obtained in the preceding paragraph (i) is immersed overnight in 10 mL of a 6 M guanidine hydrochloride/Tris solution. Next, the solution is centrifuged at 12000 rpm×10 min. to obtain a supernatant as a solubilized solution.

(iii) Metal Chelate Column

A metal chelate column carrier used is His-Bind (manufactured by Novagen). Column adjustment, sample loading and washing steps are conducted at room temperature (20° C.) according to the method recommended by the manufacturer. The His tag-fused polypeptides of interest are eluted with 60 mM imidazole/Tris solution. The results of SDS-PAGE (15% acrylamide) of the eluates demonstrated that the polypeptides exhibit a single band and are purified.

(iv) Dialysis

Imidazole is removed from the eluates by dialysis at 4° C. with 6 M guanidine hydrochloride/Tris solution as an external solution to obtain the respective polypeptide chain solutions.

(v) Refolding

Guanidine hydrochloride is removed from each of the polypeptide chain solutions of VHp-VLh and VHh-VLp by dialysis (4° C.) in the same way as above, while protein refolding is performed by steps shown below.

(a) A 6 M guanidine hydrochloride/Tris solution is used to prepare samples (volume after dilution: 10 ml) with a concentration of 7.5 μM based on the molar absorption coefficients and ΔO.D. (280 nm to 320 nm) values of the respective polypeptide chains. Next, reduction is performed at room temperature for 4 hours in the dark by the addition of β-mercaptoethanol (reducing agent) at a final concentration of 375 μM (50-fold protein concentration). These sample solutions are placed into dialysis bags (MWCO: 14,000) and used as dialysis samples.

(b) Each dialysis sample is immersed in a 6 M guanidine hydrochloride/Tris solution as an external solution for dialysis and dialyzed for 6 hours with gentle stirring.

(c) The guanidine hydrochloride concentration of the external solution is reduced in stages to 3 M and then to 2 M. The sample is dialyzed for 6 hours at each concentration of the external solution.

(d) Oxidized glutathione (GSSG) and L-Arg are added at final concentrations of 375 μM and 0.4 M, respectively, to a Tris solution. The 2 M external solution for dialysis of the paragraph (c) is added to this mixture to adjust the guanidine hydrochloride concentration to 1 M. The pH of the solution is adjusted to 8.0 (4° C.) with NaOH. The sample is dialyzed against this solution for 12 hours with gentle stirring.

(e) An L-Arg-containing Tris solution with a guanidine hydrochloride concentration of 0.5 M is prepared by the same procedures as in the paragraph (d). The sample is dialyzed against this solution for additional 12 hours.

(f) Finally, the sample is dialyzed against a Tris solution for 12 hours.

(g) After the completion of dialysis, the aggregates are separated from supernatants by centrifugation at 10000 rpm for approximately 20 minutes.

(vi) Purification of Dimerized Fraction

The individual 5 μM polypeptide (VHp-VLh and VHh-VLp) solutions obtained in the paragraph (v) are mixed and left standing overnight at 4° C. Next, a dimerized fraction corresponding to 60 kDa (approximately 18 minutes from injection) is obtained with a Sephadex 75 column (Column: buffer: 20 mM Tris and 500 mM NaCl, flow rate: 1 ml/min.). This fraction is used as a sample for interaction measurement.

Example 15

Immobilization of Photocrosslinking Group- and HEL-recognizing Complex Protein onto QCM Gold Substrate by Photocrosslinking The immobilization of the present complex protein and its ability to bind to HEL as a target substance can be evaluated by quartz crystal oscillator microbalance (QCM). A QCM apparatus used is AFFINIXQ (manufactured by INITIUM INC.).

i) Pretreatment of Substrate

First, the gold electrode surface of a QCM oscillator (manufactured by INITIUM INC.) is washed with a piranha solution (hydrogen peroxide solution:concentrated sulfuric acid=1:3) for 5 minutes×2 and washed again with distilled water. The oscillator is immersed into a solution of 1 mM dithiodipropionic acid in ethanol. The oscillator is washed with distilled water. Then, 100 mg/ml aqueous EDC (1-3-(Dimethylaminopropyl)-3-ethylcarbodiimide hydrochloride) solution and 100 mg/ml aqueous NHS (N-Hydroxysuccinimide) solution are mixed in equal amounts. A 100 μl aliquot of the obtained mixture solution is cast onto the oscillator surface. The oscillator is left for 20 minutes. Then, the oscillator is washed with 1 mM HEPES buffer (pH 8.5). Then, a 0.15 mg/ml aqueous streptavidin solution is cast onto the oscillator surface. The oscillator is left for 1 hour or longer. The oscillator is further washed with a buffer. Then, 100 μl of a 1 M aqueous ethanolamine solution is cast onto the oscillator surface. The oscillator is left for 20 minutes. Finally, buffer PBS (pH 7.4) used in binding evaluation is substituted therefor.

ii) Immobilization of Photocrosslinking Group- and HEL-Recognizing Complex Protein Onto the pretreated oscillator surface, 100 μl of a 4-(1-Azi-2,2,2-trifluoroethyl)benzoyl-Arg-Arg-NHNH-biotin solution (1 mg/ml) is cast. The oscillator is left for 1 hour or longer. The oscillator is washed with a buffer. Then, 100 μl of the photocrosslinking group- and HEL-recognizing complex protein prepared in Example 14 is cast thereonto. The oscillator is irradiated with a light with a wavelength of 365 nm at approximately 20 mW/cm$^2$ in a UV crosslinker CL-1000L (Funakoshi Corp.). The oscillator is connected to AFFINIXQ and immersed into a glass cell containing a PBS buffer to stabilize the number of frequency. The complex protein is immobilized thereon by crosslinking through light irradiation. Therefore, almost no change in the number of frequency is confirmed.

In another immobilization method, 100 μl of a 4-(1-Azi-2,2,2-trifluoroethyl)benzoic acid-BSA conjugate solution (1 mg/ml) is cast onto the EDC/NHS-treated oscillator of the paragraph i). The oscillator is left for 1 hour or longer. The oscillator is washed with a buffer. Then, 100 μl of the photocrosslinking group- and HEL-recognizing complex protein prepared in Example 14 is cast thereonto. The oscillator is irradiated with a light with a wavelength of 365 nm at approximately 20 mW/cm$^2$ in a UV crosslinker CL-1000L (Funakoshi Corp.). The oscillator is connected to AFFINIXQ and immersed into a glass cell containing a PBS buffer to stabilize the number of frequency. The complex protein is immobilized thereon by crosslinking through light irradiation. Therefore, almost no change in the number of frequency is confirmed.

Example 16

HEL Biding Evaluation Using QCM

An HEL solution is added at final concentrations of 50 nM, 200 nM and 500 nM to the glass cell. After 10 minutes, a change in each frequency is measured. A reaction rate constant is calculated from the regression line. As a result, HEL binding force can be confirmed to be sufficiently maintained in both the immobilization methods.

The exemplary embodiment of the present invention can provide a technique for immobilizing a protein having desired functions onto a substrate. Moreover, the exemplary embodiment of the present invention contributes to use of a structure including the protein immobilized on the substrate in a variety of fields such as biosensors and biomolecule purification processes. The protein according to the exemplary embodiment of the present invention can also be produced stably with microorganisms by use of genetic engineering. Moreover, the protein according to the exemplary embodiment of the present invention can be immobilized covalently with favorable orientation on a substrate. The exemplary embodiment of the present invention can provide a protein capable of crosslinking to a substrate surface through light irradiation.

The exemplary embodiment of the present invention can provide a photocrosslinking group-recognizing complex protein having one or more photocrosslinking group-binding site(s) and having a target substance-binding site, and a structure including the photocrosslinking group-recognizing complex protein immobilized on a substrate. In the structure including the photocrosslinking group-recognizing complex protein immobilized on a substrate according to the exemplary embodiment of the present invention, the protein is bound at a binding site that specifically recognizes a photocrosslinking group provided on the substrate surface, and further immobilized covalently through light irradiation. Therefore, the target substance-binding site of the protein is not immobilized on the substrate. Moreover, the protein once immobilized is not dissociated from the substrate. Furthermore, the protein is oriented homogeneously with favorable reproducibility at a distance kept from the substrate by the presence of the structural part of the photocrosslinking group-recognizing site. As a result, the target substance-binding site undergoes the minimal influence from the substrate onto the ability to bind to a target substance. Thus, the protein is immobilized efficiently with high orientation on the substrate surface. Accordingly, it is suggested that the present invention is available for achieving higher performance of products including biosensors and bioreactors, which utilize the functions of a variety of biological materials. These products utilize the physiological functions of organic matter such as biological materials immobilized on their substrate surfaces.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2006-280423, filed Oct. 13, 2006 and 2007-257738, filed Oct. 1, 2007, which are hereby incorporated by reference herein in its entirety.

What is claimed is:

1. An isolated protein comprising an anti-photocrosslinking group antibody, wherein the antibody specifically, wherein the antibody recognizes at least a photocrosslinking group, wherein the photocrosslinking group is a reactive phenyldiazirine derivative represented by the following General Formula 1:

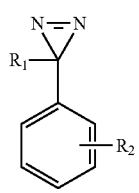

Formula 1 wherein $R_1$ represents one selected from the group consisting of a hydrogen atom and an alkyl group which may have a substituent, and $R_2$ represents one selected from the group consisting of a hydrogen atom, a halogen atom, an alkoxy group and an alkyl group which may be substituted by alkylene oxide.

2. The protein according to claim 1, wherein the anti-photocrosslinking group antibody specifically recognizes only the photocrosslinking group.

3. The protein according to claim 1, wherein the antibody is produced by a hybridoma deposited as accession No. selected from the group consisting of FERM BP-10762, FERM BP-10763, FERM BP-10764, FERM BP-10825 and FERM BP-10826 (internationally deposited de novo).

4. The protein according to claim 1, wherein the antibody has complementarity-determining regions comprising amino acid sequences of any of the following (a) to (d) or complementarity-determining regions functionally equivalent thereto:
   (a) amino acid sequences comprising sequences of SEQ ID NOs: 1, 2 and 3;
   (b) amino acid sequences comprising sequences of SEQ ID NOs: 4, 5 and 6;
   (c) amino acid sequences comprising sequences of SEQ ID NOs: 7, 8 and 9; and
   (d) amino acid sequences comprising sequences of SEQ ID NOs: 10, 11 and 12.

5. The protein according to claim 1, wherein the antibody is selected from the group consisting of a chimeric antibody, a complementarity-determining region-grafted antibody, a single-chain antibody and antibody fragments thereof.

6. An isolated protein capable of binding to a target substance, comprising:
   at least one first region that recognizes at least a photocrosslinking group; and
   at least one second region that recognizes the target substance,
   wherein the first region comprises an anti-photocrosslinking group antibody specifically recognizing the photocrosslinking group,
   wherein the photocrosslinking group is a reactive phenyldiazirine derivative represented by the following General Formula 1:

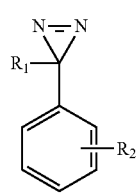

Formula 1 wherein $R_1$ represents one selected from the group consisting of a hydrogen atom and an alkyl group which may have a substituent, and $R_2$ represents one selected from the group consisting of a hydrogen atom, a halogen atom, an alkoxy group and an alkyl group which may be substituted by alkylene oxide, and
   wherein the target substance recognized by the second region is different from the photocrosslinking group.

7. A method for immobilizing the protein according to claim 1 onto a substrate, comprising:
   1) providing a substrate surface with the photocrosslinking group;
   2) reacting the protein with the photocrosslinking group on the substrate surface by use of the ability of the antibody to specifically recognize the photocrosslinking group so as to immobilize the protein onto the substrate; and 3) irradiating the substrate with light after or simultaneously with the reaction so as to form a crosslinked structure between the substrate and the protein through a photocrosslinking reaction using the photocrosslinking group.

8. A structure comprising a substrate and a protein according to claim 1, wherein the substrate has the photocrosslinking group on at least a portion of the surface of the substrate.

9. A biosensor comprising a structure according to claim 8.

10. An isolated nucleic acid encoding a protein according to claim 1.

11. A vector comprising a nucleic acid according to claim 10.

12. A detecting kit for detecting a target substance, comprising a substrate and a protein for forming a structure according to claim 8.

* * * * *